US011207081B2

(12) United States Patent
Voor et al.

(10) Patent No.: US 11,207,081 B2
(45) Date of Patent: Dec. 28, 2021

(54) SYSTEMS AND METHODS FOR INTRAMEDULLARY PREPARATIONS

(71) Applicant: University of Louisville Research Foundation, Inc., Louisville, KY (US)

(72) Inventors: Michael Voor, Louisville, KY (US); David Seligson, Louisville, KY (US); Richard Joseph Ackermann, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 236 days.

(21) Appl. No.: 16/343,185

(22) PCT Filed: Oct. 20, 2017

(86) PCT No.: PCT/US2017/057653
§ 371 (c)(1),
(2) Date: Apr. 18, 2019

(87) PCT Pub. No.: WO2018/075925
PCT Pub. Date: Apr. 26, 2018

(65) Prior Publication Data
US 2019/0239899 A1 Aug. 8, 2019

Related U.S. Application Data

(60) Provisional application No. 62/411,103, filed on Oct. 21, 2016.

(51) Int. Cl.
*A61B 17/16* (2006.01)
*A61B 17/58* (2006.01)
(Continued)

(52) U.S. Cl.
CPC ........ *A61B 17/164* (2013.01); *A61B 17/1622* (2013.01); *A61B 17/1631* (2013.01);
(Continued)

(58) Field of Classification Search
CPC . A61B 17/16; A61B 17/1622; A61B 17/1624; A61B 17/1626; A61B 17/1628;
(Continued)

(56) References Cited

U.S. PATENT DOCUMENTS 3,835,858 A * 9/1974 Hagen ................ A61B 17/1633
606/180
4,646,738 A 3/1987 Trott
(Continued)

FOREIGN PATENT DOCUMENTS

EP 2 371 304 A1 10/2011
EP 2 777 570 A1 9/2014
(Continued)

OTHER PUBLICATIONS

International Preliminary Report on Patentability, Written Opinion, and International Search Report for Application No. PCT/US2017/057653 dated Dec. 27, 2017.
(Continued)

*Primary Examiner* — Eric S Gibson
(74) *Attorney, Agent, or Firm* — Jenkins, Wilson, Taylor & Hunt, P.A.

(57) ABSTRACT

A system for intramedullary preparations comprises a directional reamer including a flexible drive shaft having a proximal end and a distal end, and a cutting head operably connected to the distal end of the flexible drive shaft. The system further includes a means of displacing the distal end of the flexible drive shaft and deflecting the cutting head to selectively shape a medullary canal in a bone. A follower sleeve is also include in the system and has a proximal end and a distal end in the form of a collar, with the follower sleeve being configured to accept the flexible drive shaft. The system additionally includes a reaming plunger that extends through the follower sleeve and is positioned adja-
(Continued)

cent to the flexible drive shaft such that the reaming plunger engages the collar of the follower sleeve to deflect the cutting head.

24 Claims, 17 Drawing Sheets

(51) Int. Cl.
    *A61B 17/56*     (2006.01)
    *A61B 17/17*     (2006.01)
    *A61B 17/00*     (2006.01)

(52) U.S. Cl.
    CPC ...... *A61B 17/1633* (2013.01); *A61B 17/1659* (2013.01); *A61B 17/1717* (2013.01); *A61B 17/56* (2013.01); *A61B 17/58* (2013.01); *A61B 17/1626* (2013.01); *A61B 2017/00367* (2013.01); *A61B 2217/005* (2013.01)

(58) Field of Classification Search
    CPC ............ A61B 17/1631; A61B 17/1633; A61B 17/164
    See application file for complete search history.

(56) References Cited

U.S. PATENT DOCUMENTS

| | | | |
|---|---|---|---|
| 5,062,845 A | 11/1991 | Kuslich et al. | |
| 5,431,671 A | 7/1995 | Nallakrishnan | |
| 5,591,170 A | 1/1997 | Spievack et al. | |
| 5,622,434 A * | 4/1997 | Takahashi | F16C 31/04 384/49 |
| 5,716,140 A * | 2/1998 | Kondo | F16C 29/04 384/49 |
| 5,908,423 A * | 6/1999 | Kashuba | A61B 17/164 606/80 |
| 5,928,239 A | 7/1999 | Mirza | |
| 6,332,886 B1 * | 12/2001 | Green | A61B 17/1617 606/80 |
| 6,383,188 B2 | 5/2002 | Kuslich et al. | |
| 7,749,225 B2 | 7/2010 | Chappuis et al. | |
| 10,631,876 B2 * | 4/2020 | Machill | F16C 33/40 |
| 2003/0219184 A1 * | 11/2003 | Rio | A61B 17/1624 384/523 |
| 2005/0283175 A1 | 12/2005 | Tanner et al. | |
| 2006/0161191 A1 * | 7/2006 | Bucina | A61B 17/32002 606/180 |
| 2009/0326538 A1 | 12/2009 | Sennett et al. | |
| 2010/0042104 A1 | 2/2010 | Kota et al. | |
| 2010/0076503 A1 | 3/2010 | Beyar et al. | |
| 2011/0208194 A1 * | 8/2011 | Steiner | A61B 17/1764 606/80 |
| 2011/0295261 A1 | 12/2011 | Germain | |
| 2013/0023900 A1 * | 1/2013 | Nishio | B23B 39/14 606/130 |
| 2013/0204255 A1 * | 8/2013 | Milburn | A61B 17/14 606/82 |
| 2013/0274749 A1 * | 10/2013 | Ye | A61B 17/16 606/79 |
| 2014/0171948 A1 | 6/2014 | Griffiths et al. | |
| 2014/0236156 A1 * | 8/2014 | Arlettaz | A61B 17/164 606/80 |
| 2014/0309636 A1 * | 10/2014 | Meek | A61B 17/164 606/62 |
| 2016/0199072 A1 | 7/2016 | Torrie et al. | |
| 2018/0360475 A1 * | 12/2018 | Kohler | A61B 17/1633 |
| 2019/0015112 A1 * | 1/2019 | Machill | A61B 17/144 |
| 2019/0069908 A1 * | 3/2019 | Zilberman | A61B 17/1631 |
| 2019/0125371 A1 * | 5/2019 | Asfora | A61B 17/864 |
| 2019/0239899 A1 * | 8/2019 | Voor | A61B 17/56 |
| 2019/0343568 A1 * | 11/2019 | Childers | A61B 17/162 |
| 2020/0375615 A1 * | 12/2020 | Walker | A61B 17/1764 |

FOREIGN PATENT DOCUMENTS

| | | |
|---|---|---|
| EP | 3 000 417 A1 | 3/2016 |
| WO | WO 2011/137377 A1 | 11/2011 |
| WO | WO 2015/050940 A1 | 4/2015 |
| WO | WO 2018/075925 A1 | 4/2018 |

OTHER PUBLICATIONS

European Search Report for Application No. 17862808.7 dated Jun. 30, 2020.

* cited by examiner

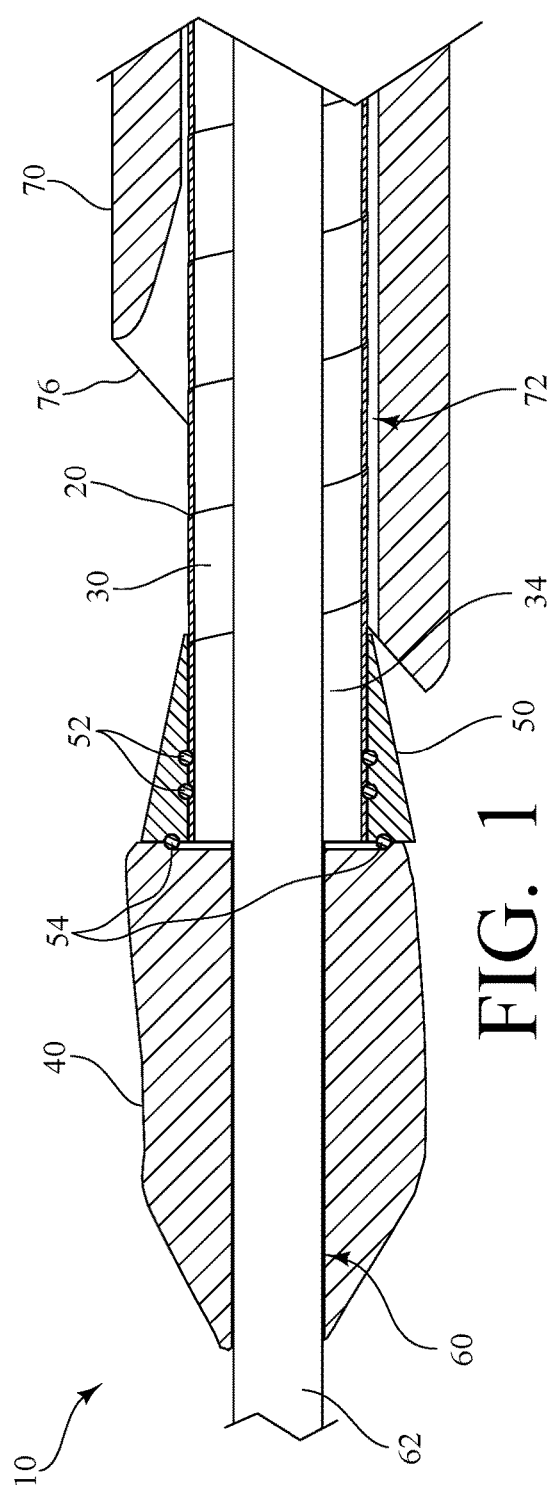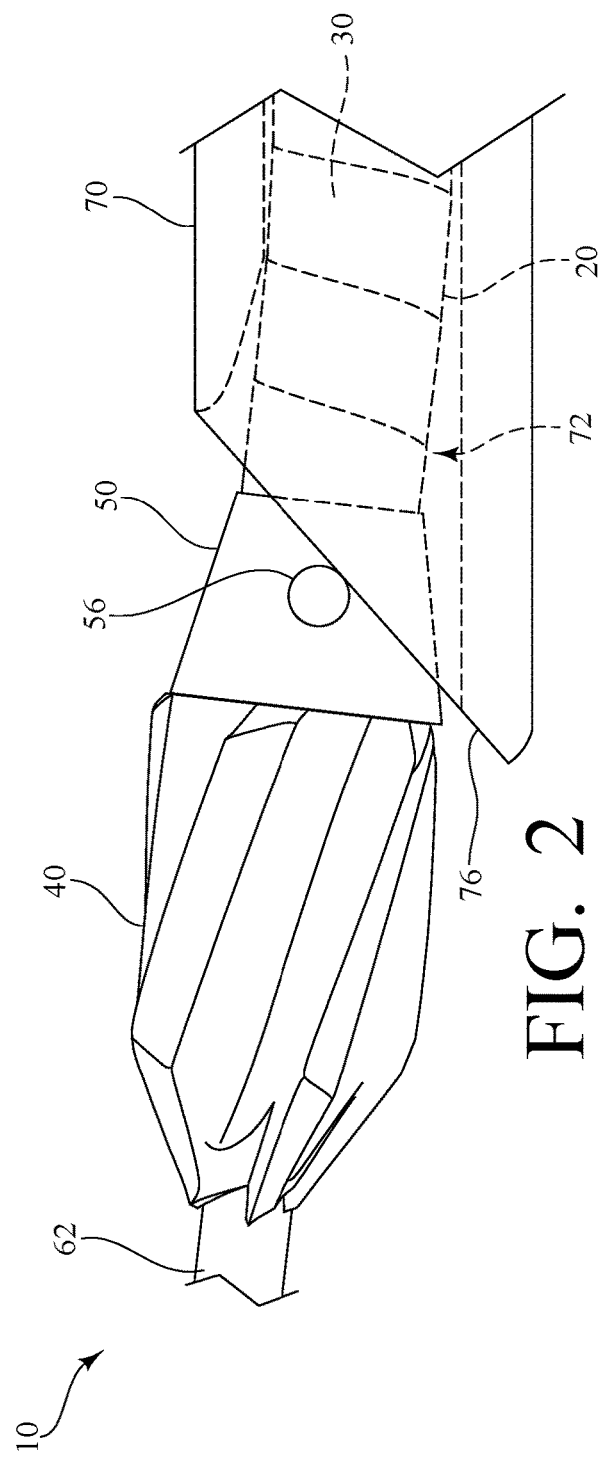

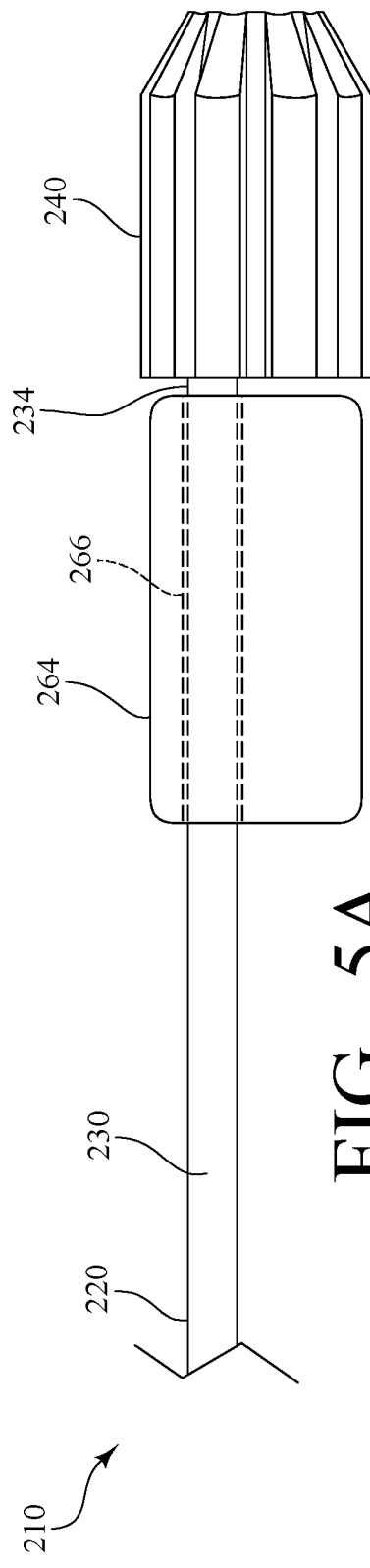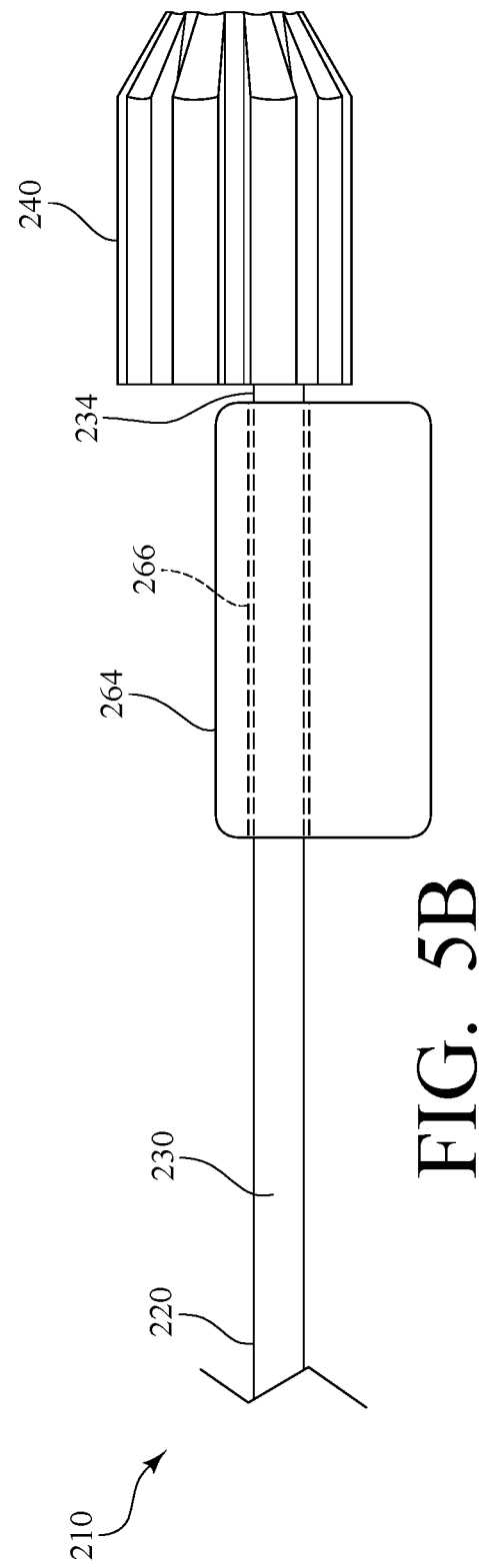

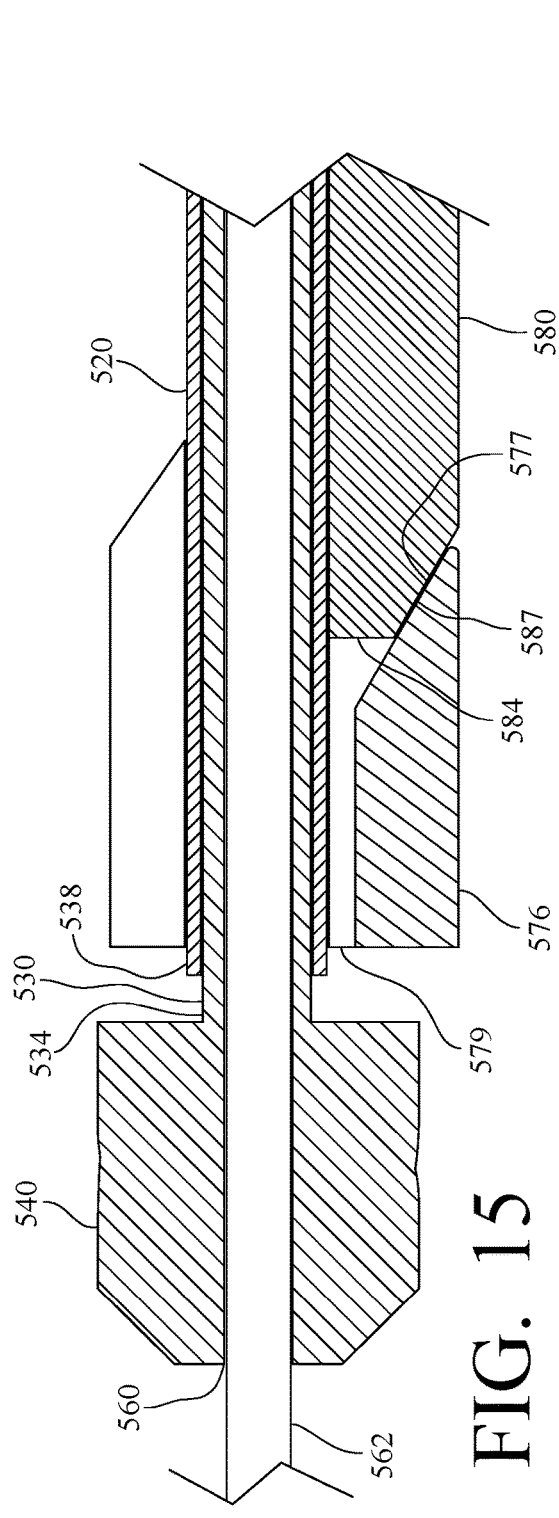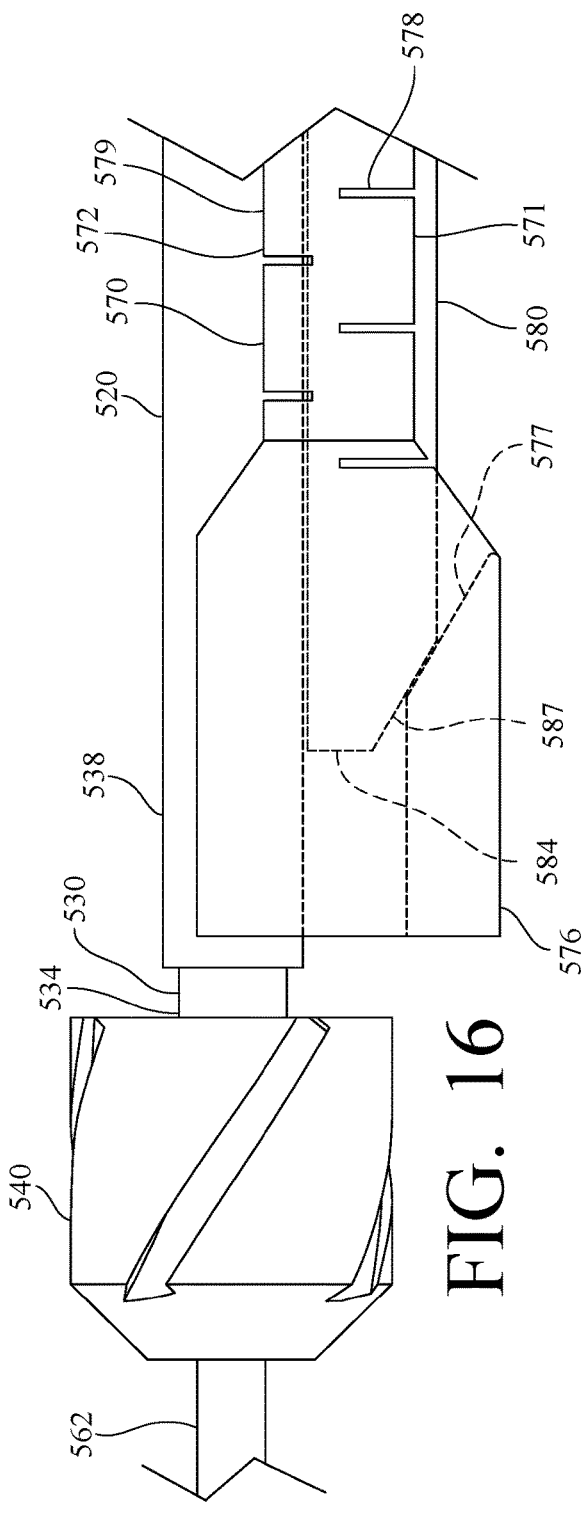
FIG. 15
FIG. 16

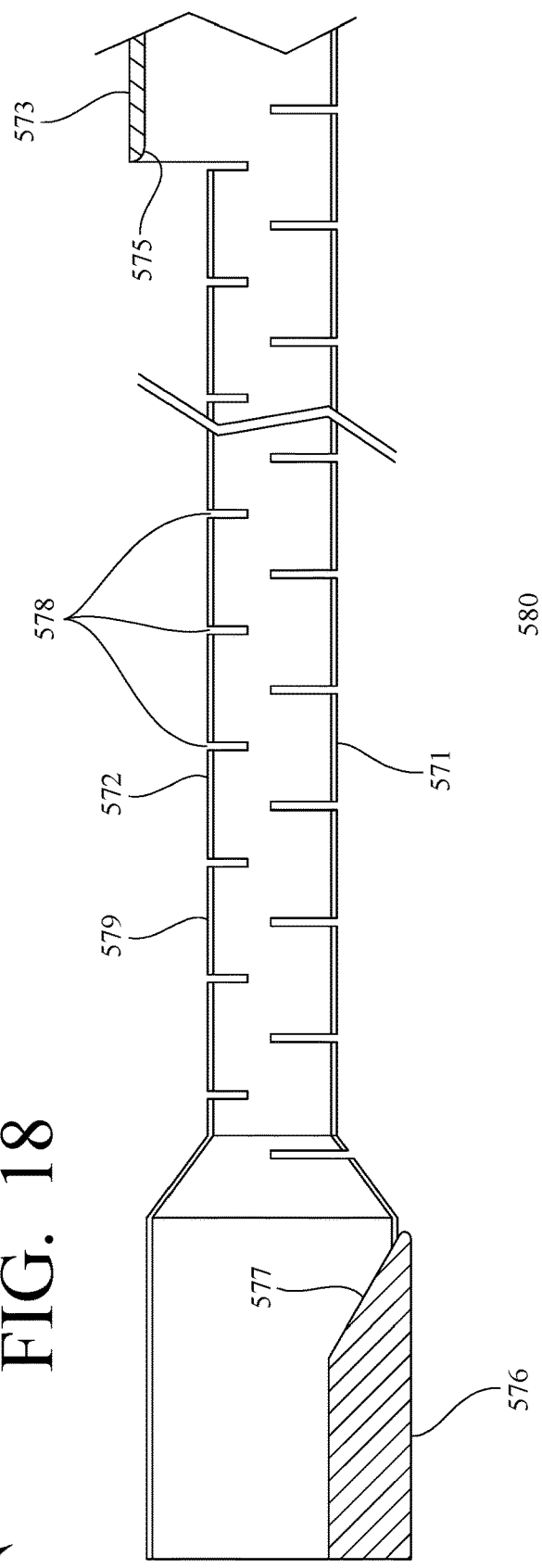
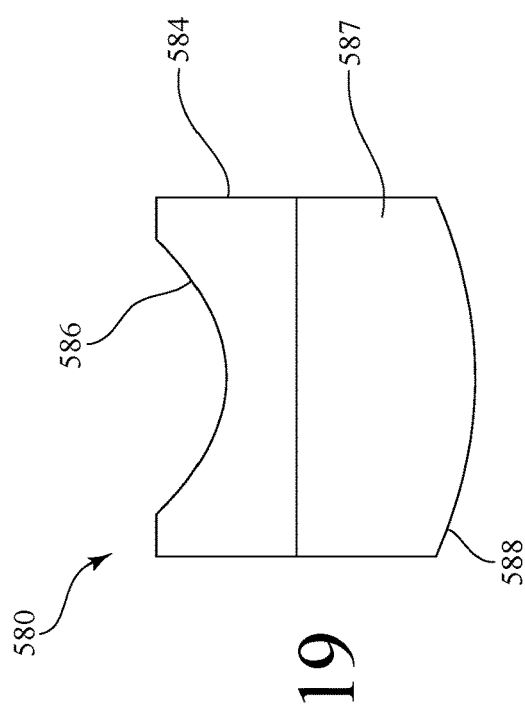
FIG. 18
FIG. 19

SYSTEMS AND METHODS FOR INTRAMEDULLARY PREPARATIONS

CROSS-REFERENCE TO RELATED APPLICATIONS

The present application claims priority to U.S. Patent Application Ser. No. 62/411,103 filed on Oct. 21, 2016, the entire disclosure of which is incorporated herein by reference.

TECHNICAL FIELD

The present invention relates to systems and methods for intramedullary preparations. In particular, the present invention relates to systems and methods for intramedullary preparations that make use of a directional reamer to selectively shape a medullary canal in a bone.

BACKGROUND

Intramedullary (IM) nailing of long bone fractures is one of several methods used by orthopedic surgeons to provide mechanical stability to a healing bone and, in recent years, has become the gold standard that is used whenever a specific fracture pattern allows. During IM nailing, the medullary canal is enlarged with reamers placed over a guide wire along the length of the marrow space of a long bone, such as the femur, tibia, or humerus. These reamers are typically manufactured in ½ mm diameter steps and are typically used in multiple passes to form or enlarge a canal within the medullary cavity of the bone. The resulting enlargement of the canal then creates a smooth, hollow tube of constant minimum diameter that allows thicker, more rigid IM nails to subsequently be used for fracture fixation.

Despite the advantages associated with the use of IM nailing for long bone fractures, a frequently encountered issue is that not all fractures have simple geometries. Bone fracture fragments can frequently lie out of their original position in the bone and heal partially in place. Moreover, often the shape of a bone is neither tubular nor symmetric. For example, the bone shaft may be thicker anteriorly than posteriorly. In such a case, selective shaping of the medullary cavity or marrow space (i.e., medullary shaping) would allow for removal of bone where it is not needed while retaining the thickness of bone on the thinner side. As another example, a tibial nonunion may benefit from primary nail removal, directional reaming, and canal widening at the level of the nonunion, followed by bone graft introduction internally and secondary nailing. Of course, there are numerous other types of fractures cases in which a non-union or a primarily treated fracture would benefit from selective canal shaping followed by targeted bone grafting. To date, however, such fracture cases are usually handled by changing the procedure entirely or by performing an open reduction and internal fixation. Accordingly, there remains a need in the art for systems and methods that can be used to shape an intramedullary canal in a bone.

SUMMARY

The present invention relates to a system for intramedullary preparations that, in some embodiments includes a directional reamer, a follower sleeve, and a reaming plunger. The directional reamer includes a flexible drive shaft having a proximal end and a distal end, and a cutting head operably connected to the distal end of the flexible drive shaft. The follower sleeve has a proximal end and a distal end in the form of a collar, and the follower sleeve defines a channel configured to accept the flexible drive shaft. The reaming plunger extends through the channel of the follower sleeve and is positioned adjacent to the flexible drive shaft such that the reaming plunger engages the collar of the follower sleeve to displace the distal end of the flexible drive shaft and deflect the cutting head. More specifically, in some embodiments of the present invention, the collar defines a first sloped surface and the reaming plunger defines a second sloped surface that engages the first sloped surface such that, when the reaming plunger is advanced along the channel, the second sloped surface slides along the first sloped surface causing the reaming plunger to move outward within the channel of the follower sleeve. In some embodiments, the collar containing the first sloped surface must remain in place in the bony canal so the reamer can be displaced by the reaming plunger. Thus, in some embodiments, the collar is advantageously configured such that the outer surface of the collar engages the inner surface of a bony canal such that it does not slip rotationally during reaming. In some embodiments, that prevention of rotation is accomplished via longitudinal flutes on the outer surface of the collar.

In some embodiments of the present invention, the flexible drive shaft and the cutting head collectively define an internal cannula that extends through the flexible drive shaft from the proximal end to the distal end of the flexible drive shaft and through the cutting head. In some embodiments, such an internal cannula has a diameter sufficient to surround a guide wire.

Furthermore, in some embodiments of the present invention, the reaming plunger defines a concave upper surface such that the flexible drive shaft rests partially within the concave upper surface. In other embodiments of the present invention, the reaming plunger further includes a cover pad positioned on an upper surface of the reaming plunger such that the flexible drive shaft rests on the cover pad.

With respect to the follower sleeve, in some embodiments of the present invention, the channel of the follower sleeve has an open bottom along substantially the entire length of the follower sleeve and an open top along substantially the entire length of the follower sleeve with one or more bands spanning across the open top of the channel. In some embodiments having one or more bands, at least one of the one or more bands includes a fluted forward edge configured to engage the flexible drive shaft when the reaming plunger displaces the distal end of the flexible drive shaft and deflects the cutting head.

In some embodiments of the present invention, the system further comprises a drill connected to the proximal end of the flexible drive shaft. Additionally, in some embodiments, the system further comprises a handle operably attached to the follower sleeve and configured to advance the reaming plunger relative to the follower sleeve to thereby deflect the cutting head of the directional reamer. In some embodiments, such a handle includes a lever for advancing the reaming plunger with the lever including an upper portion secured to a proximal end of the reaming plunger. Furthermore, in some embodiments, the handle also includes a locking mechanism to maintain the position of the lever.

Further provided in some embodiments of the present invention are methods for fixing a bone in a subject. In some embodiments, an exemplary method for fixing a bone in a subject includes first providing a directional reamer, the directional reamer including a flexible drive shaft have a proximal end and a distal end and a cutting head operably connected to the distal end of the flexible drive shaft. A follower sleeve extending from a handle and terminating at a collar is then provided, with the follower sleeve defining a channel configured to accept the flexible drive shaft. A reaming plunger is then provided that extends through the channel of the follower sleeve and is positioned below the flexible drive shaft. The flexible drive shaft is then inserted into the channel of the follower sleeve such that the cutting head extends forward of the collar. Upon initial placement into a medullary canal, and depending on the overall anatomy of the bone or the geometry of a particular bone fracture being treated, the reaming plunger is then selectively advanced along the channel of the follower sleeve such that a distal end of the reaming plunger engages the collar of the follower sleeve to displace the distal end of the flexible drive shaft. This, in turn, deflects the cutting head of the directional reamer to the extent desired.

Further features and advantages of the presently-disclosed subject matter will become evident to those of ordinary skill in the art after a study of the description, figures, and non-limiting examples in this document.

BRIEF DESCRIPTION OF THE DRAWINGS

FIG. 1 is a partial cross-sectional view of a system for intramedullary preparation made in accordance with the present invention and including a directional reamer and a follower sleeve;

FIG. 2 is a partial side view of the system of FIG. 1, but showing the cutting head of the directional reamer deflected by the follower sleeve;

FIG. 5A is a partial side view of another system for intramedullary preparation made in accordance with the present invention including an eccentrically mounted cutting head;

FIG. 5B is a partial side view of the system of FIG. 5A showing the cutting head rotated into a different position relative to the cam guide;

FIG. 15 is a partial cross-sectional view of another system for intramedullary preparation made in accordance with the present invention and including a directional reamer, a reaming plunger, and a follower sleeve;

FIG. 16 is a partial side view of the distal end of the system of FIG. 15, but showing the cutting head of the directional reamer deflected by the reaming plunger;

FIG. 18 is a partial side sectional view of the follower sleeve of FIG. 15 with portions of the follower sleeve removed to show more of its length;

FIG. 19 is a front view of the plunger of FIG. 15;

DESCRIPTION OF EXEMPLARY EMBODIMENTS

The present invention includes systems and methods for intramedullary preparations. In particular, the present invention include systems and methods for intramedullary preparations that make use of a directional reamer to selectively shape a medullary canal in a bone.

Figure 3:
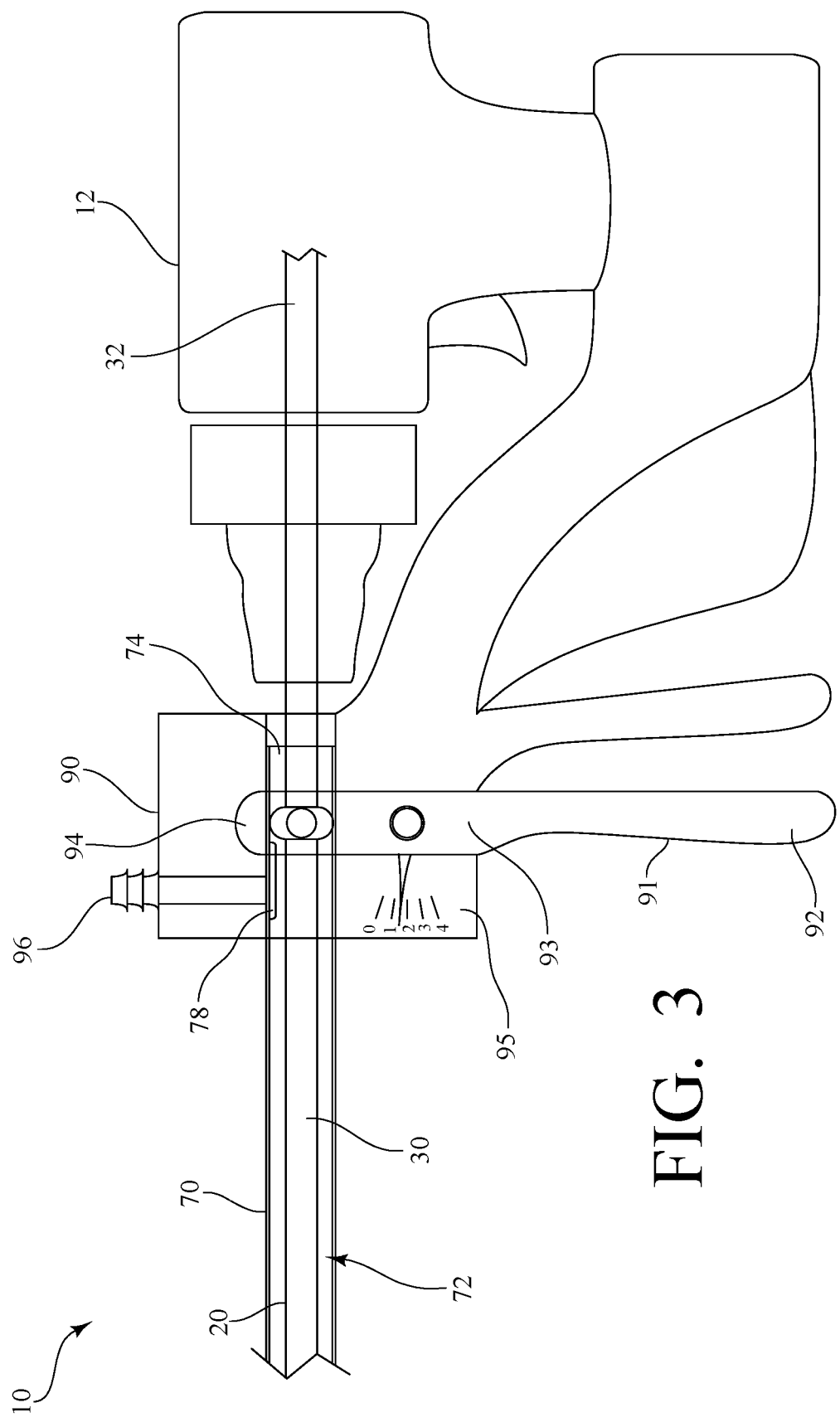
FIG. 3 is another partial side view of the system of FIG. 1, but showing the proximal ends of the directional reamer and the follower sleeve connected to an indexing unit and a drill.

Referring first to FIGS. 1-3, in one exemplary embodiment of the present invention, a system 10 for intramedullary preparations is provided that includes a directional reamer 20 and a follower sleeve 70. The directional reamer 20 includes a flexible drive shaft 30 having a proximal end 32 (shown in FIG. 3) and a distal end 34 (shown in FIG. 1), with a cutting head 40 operably connected to the distal end 34 of the flexible drive shaft 30. The directional reamer 20 further includes a conical roller bearing 50 operably connected to the distal end 34 of the flexible drive shaft 30 adjacent to the cutting head 40. The conical roller bearing 50 has a first set of rollers 52 operably connected to the flexible drive shaft 30 to allow the flexible drive shaft 30 to rotate freely within the conical roller bearing 50, and a second set of rollers 54 operably connected to the cutting head 40 to allow the cutting head 40 to rotate against the conical roller bearing 50. The conical roller bearing 50 also has an exterior post 56 to facilitate the deflection of the cutting head 40 during use, as described in further detail below.

To further allow the directional reamer 20 to be effectively used to form a medullary canal in a bone, the flexible drive shaft 30 and the cutting head 40 of the directional reamer 20 collectively define an internal cannula 60 that extends through the flexible drive shaft 30 from the proximal end 32 to the distal end 34 of the flexible drive shaft 30 and through the cutting head 40. In this regard, the internal cannula 60 has a diameter sufficient to surround a guide wire 62 typically used in IM nailing of long bone fractures (e.g., a flexible 3.5 mm guide wire), as shown in FIGS. 1 and 2.

Referring still to FIGS. 1-3, as noted, the exemplary system 10 for intramedullary preparations also includes a follower sleeve 70 that has a beveled distal end 76 for contacting the conical roller bearing 50 and a proximal end 74 for attaching to a handle 90, as also described further below. The follower sleeve 70 further includes one or more fenestrations 78 and defines a hollow interior 72 having a diameter sufficient for clearing any reaming debris without significant pressure buildup and sufficient for surrounding the flexible drive shaft 30 of the directional reamer 20. In this regard, by surrounding the flexible drive shaft 30 of the directional reamer 20 with the follower sleeve 70, the follower sleeve 70 can be advanced along the length of the directional reamer 20 to deflect the cutting head 40 of the directional reamer 20 and provide selective shaping of an intramedullary canal by varying the amount of deflection experienced by the cutting head 40. More specifically, in the exemplary system 10, as the follower sleeve 70 is advanced along the length of the directional reamer 20, the beveled distal end 76 of the follower sleeve 70 contacts the exterior post 56 of the conical roller bearing 50 and begins to deflect the cutting head 40 of the directional reamer 20. Then, if the follower sleeve 70 continues to be advanced along the length of the directional reamer 20, the exterior post 56 slides along the beveled distal end 76 of the follower sleeve 70 and results in a greater degree of deflection of the cutting head 40.

With respect to the dimensions of the exemplary system 10, including the directional reamer 20 and the follower sleeve 70, each of the components will typically have a diameter of less than 12 mm, such that, upon assembly, each of the components will fit within a 12 mm diameter cylindrical space inside the intramedullary canal. In operation, however, in some embodiments and by making use of a flexible directional reamer 20 and the follower sleeve 70 that allows for deflection of the cutting head 40, the system 10 can be configured such that the system 10 is capable of reaming beyond a 12 mm diameter (i.e., a 6 mm radius) at any specified length along the medullary canal being formed. For instance, in some embodiments, the system 10 can be configured to allow reaming in only one lateral direction to any radius between 6 and 9 mm, completely circumferentially to any radius between 6 and 9 mm, or over any arc-length in between (e.g., partially circumferential reaming between 6 and 9 mm radius).

Figure 4:
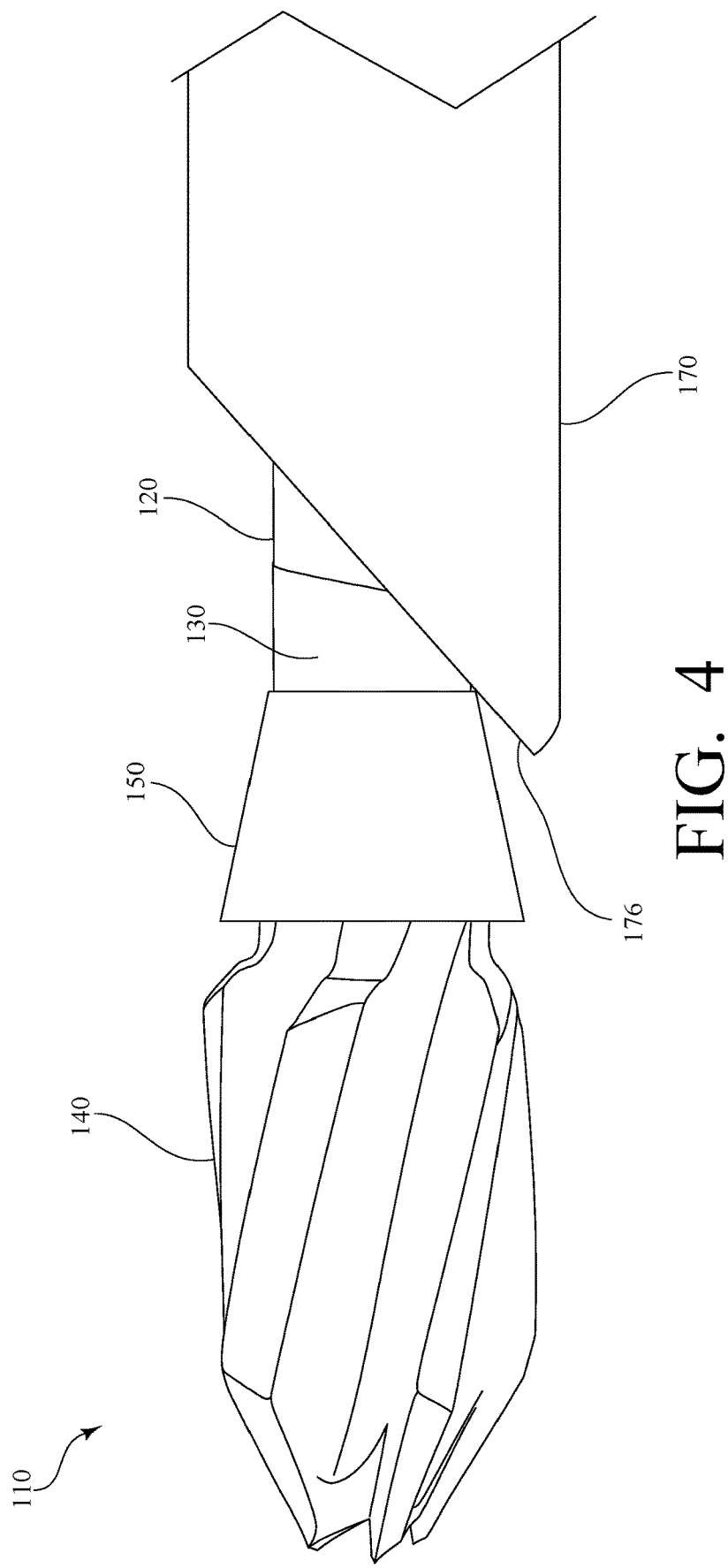
FIG. 4 is a partial side view of another system for intramedullary preparation made in accordance with the present invention.

As a refinement, in another embodiment of the present invention that makes use of a follower sleeve having a beveled distal end, and referring now to FIG. 4, an exemplary system 110 for intramedullary preparation is provided that includes a directional reamer 120 including a flexible drive shaft 130, a cutting head 140, and a conical roller bearing 150. The system 110 also includes a follower sleeve 170 that surrounds the flexible drive shaft 130 of the directional reamer 120 and that includes a beveled distal end 176 to deflect the cutting head 140. Unlike the exemplary system 10 shown in FIGS. 1-3, however, the conical roller bearing 150 does not make use of an exterior post for contacting the beveled distal end 176 of the follower sleeve 170. Rather in the exemplary system 110 shown in FIG. 4, the beveled distal end 176 of the follower sleeve 170 directly contacts the conical roller bearing 150 to deflect the cutting head 140 of the directional reamer 120, while the cutting head 140 is spaced slightly away from the conical roller bearing 150 to prevent the beveled distal end 176 of the follower sleeve 170 from contacting the cutting head 140 as the follower sleeve 170 is advanced.

Regardless of the particular configuration of the conical roller bearing used in accordance with the present invention, and referring again to FIGS. 1-3, to form an intramedullary canal in a bone, the system 10 for intramedullary preparation further includes a standard orthopedic drill 12 (e.g., a rotary drill) or orthopedic reamer driver that is configured to connect to the proximal end 32 of the directional reamer 20 and that is used to rotate the directional reamer 20 within the follower sleeve 70. To provide a further amount of control over the deflection of the cutting head 40 of the directional reamer 20, however, the system 10 further comprises a handle 90 that is operably attached to the follower sleeve 70 and that is used to controllably advance the follower sleeve 70 along the length of the flexible drive shaft 30 to thereby deflect the cutting head 40 of the directional reamer 20. The handle 90 includes a lever 91 for advancing the follower sleeve 70, with the lever 91 including a lower portion 92, a central portion 93 pivotally connected to the remainder of the handle 90 and an upper portion 94 secured to the proximal end 74 of the flexible sleeve 70. In this regard, as the lower portion 92 of the lever 91 is pulled toward the drill 12 of the system 10, the upper portion 94 of the lever 91 and, consequently, the follower sleeve 70 is advanced laterally away from the drill 12 to thereby deflect the cutting head 40 of the directional reamer 20 as described above.

The handle 90 can further be used as an indexing unit. To control the amount of advancement of the follower sleeve 70 as a result of the movement of the upper portion of 94 of the lever 91, the system 10 further includes a controller 95 that is operably connected to the lever 91. For example, in certain embodiments, to control the amount of advancement of the follower sleeve 70, the controller 95 is configured to only allow the lower portion 92 of the lever 91 to be moved toward the drill 12 a predetermined distance and, as a result, only allow the upper portion 94 of the lever 91 to advance the follower sleeve 70 a distance that is in direct relation to that predetermined distance.

As an even further refinement to the present invention, to allow the systems for intramedullary preparation made in accordance with the present invention to be more effectively used for the selective shaping of an intramedullary canal, and referring still to FIGS. 1-3, as previously mentioned, the follower sleeve 70 defines one or more fenestrations 78 for removing biological material from the hollow interior 72 of the follower sleeve 70. In this embodiment, the handle 90 thus further includes a port 96 that is configured to be in fluid communication with the one or more fenestrations 78 of the follower sleeve 70 (i.e., upon attachment of the follower sleeve 70 to the handle 90), and that is further configured to be connected to a suction to remove the biological material away from the system 10.

As yet another refinement, in a further embodiment of the present invention that makes use of a reamer for intramedullary preparations, and referring now to FIGS. 5A and 5B, an exemplary system 210 for intramedullary preparation is provided that includes a reamer 220 having a drive shaft 230 and a cutting head 240 mounted to the distal end 234 of the drive shaft 230. Unlike the exemplary systems shown in FIGS. 1-4, however, the cutting head 240 is not centrally mounted on the drive shaft 230 such that the lateral distances from the center of the cutting head 240 to its lateral, outer edges are equal. Rather, in the system 210, the cutting head 240 is eccentrically mounted to the distal end 234 of the drive shaft 230. In this regard, the system 210 also includes a cam guide 264 defining a hollow interior 266 that has a diameter sufficient for surrounding the drive shaft 230 of the reamer 220. The cam guide 264 also has a width that allows the eccentrically mounted cutting head 240 to be inserted into an intramedullary canal having a given diameter, as shown best in FIG. 5A. Then, once the cutting head 240 is placed in a desired location, the cutting head 240 can then be rotated to shape an intramedullary canal in a bone, as shown best in FIG. 5B. With further respect to such eccentric mounting of a cutting head, it is also contemplated that, in other similar embodiments, multiple cutting heads having multiple different diameters can be included in such systems to increase the lateral eccentricity of an intramedullary canal in a stepwise manner.

Figure 6:
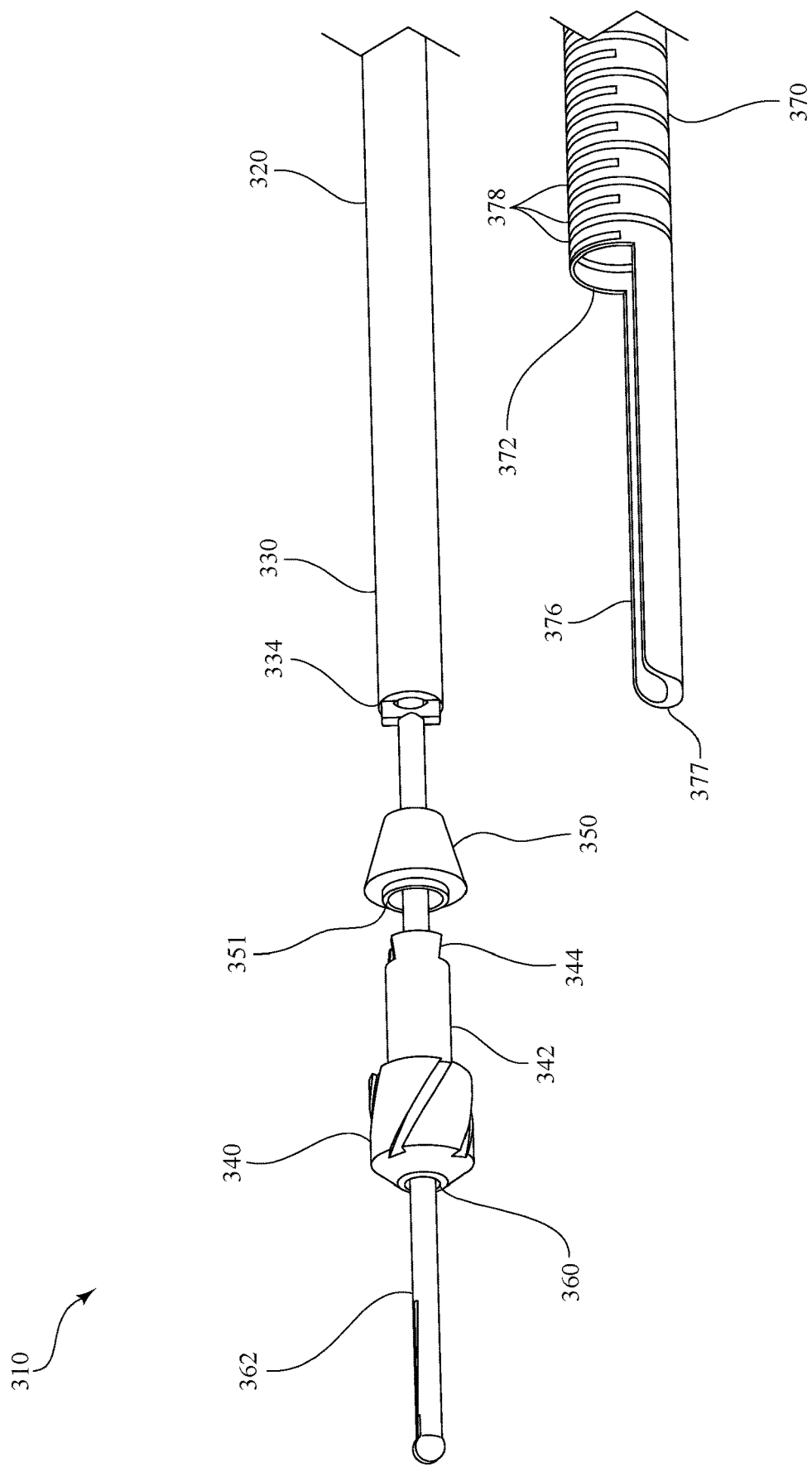
FIG. 6 is a partial exploded perspective view of another system for intramedullary preparation made in accordance with the present invention and showing the distal end of a directional reamer and a follower sleeve.
Figure 10:
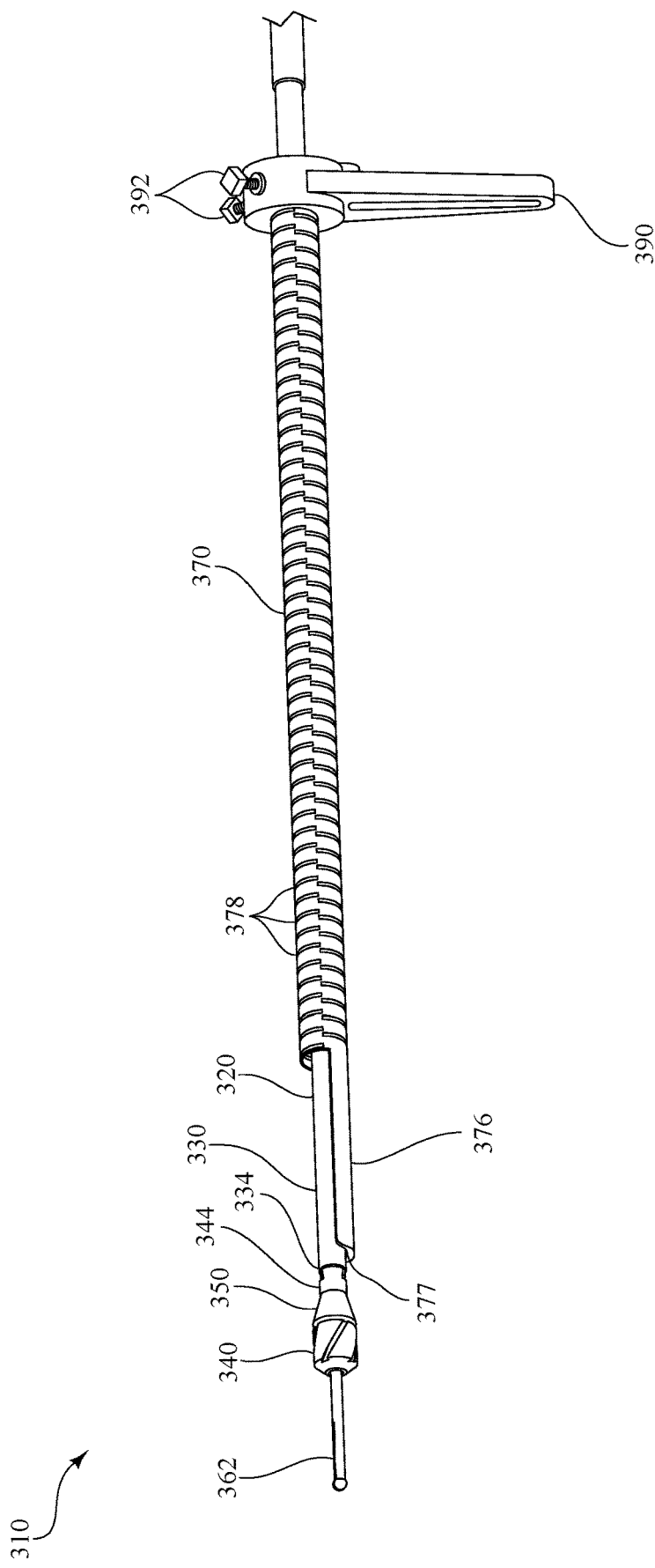
FIG. 10 is a perspective view of the system of FIG. 6 and also showing a handle for controlling the follower sleeve.

As a further refinement, in a further embodiment of the present invention that makes use of a follower sleeve, and referring now to FIGS. 6 and 10, an exemplary system 310 for intramedullary preparation is provided that includes a directional reamer 320 including a flexible drive shaft 330, a cutting head 340, and a conical bearing 350 (e.g., a roller bearing). The system 310 also includes a follower sleeve 370 that surrounds the flexible drive shaft 330 of the directional reamer 320 and that includes a distal end to deflect the cutting head 340. Unlike the exemplary system 10 shown in FIGS. 1-3, however, the distal end of the follower sleeve 370 is not beveled, but is instead comprised of a curved panel 376.

Figure 7A:
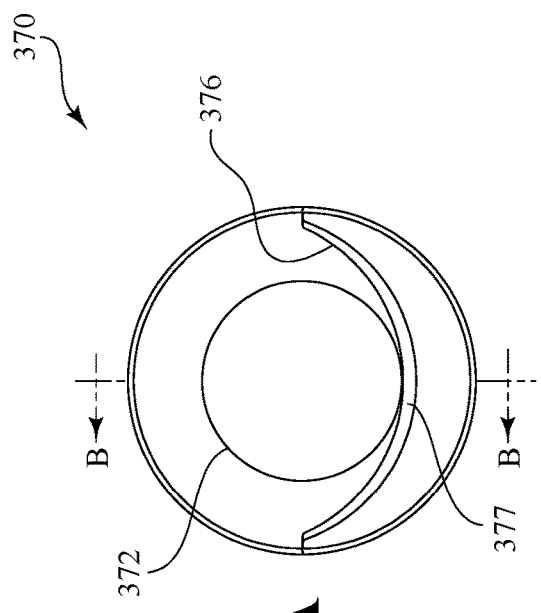
FIG. 7A is a front view of the follower sleeve of FIG. 6.
Figure 7B:
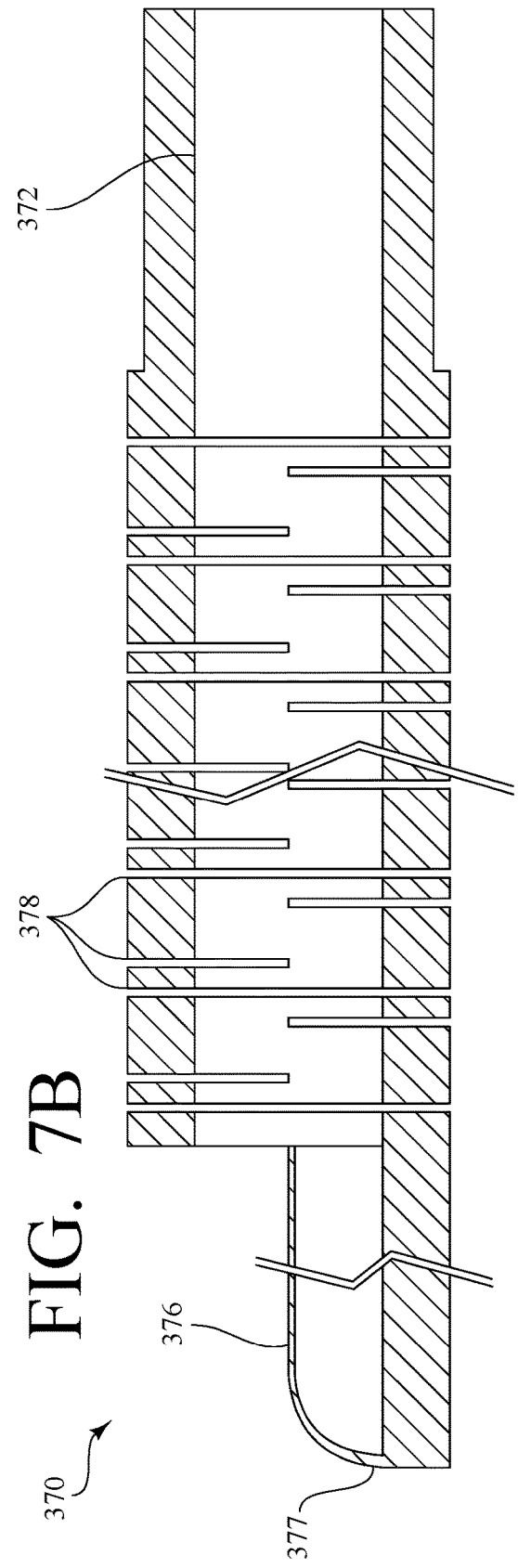
FIG. 7B is side sectional view of the follower sleeve taken along line B-B of FIG. 7A with portions of the follower sleeve removed to show its entire length.

In particular, and referring now to FIGS. 7A and 7B, the curved panel 376 has an exterior surface that is effectively a continuous extension of the exterior surface of the remainder of the follower sleeve 370 and an interior surface that mates with a hollow interior 372 of the follower sleeve 370. Similar to the exemplary system 110 shown in FIG. 4, the conical bearing 350 does not make use of an exterior post for contacting the curved panel 376 of the follower sleeve 370. Instead, in the exemplary system 310, a leading edge 377 of the interior surface of the curved panel 376 directly contacts the conical bearing 350 to deflect the cutting head 340 of the directional reamer 320. The semi-circular design of the curved panel 376 provides the necessary room for the conical bearing 350 and cutting head 340 to deflect without any concern of the cutting head 340 contacting the remainder of the follower sleeve 370. The follower sleeve 370 further includes a plurality of quadrant cuts (or fenestrations) 378 along the length of the follower sleeve 370, which are in communication with the hollow interior 372 of the follower sleeve 370 and which provide the follower sleeve 370 an amount of flexibility to accommodate a curved femur. In some embodiments, the follow sleeve 370 can further include longitudinal fluting (not shown) in the follower sleeve to help clear any reaming debris from the hollow interior 372.

Figure 8:
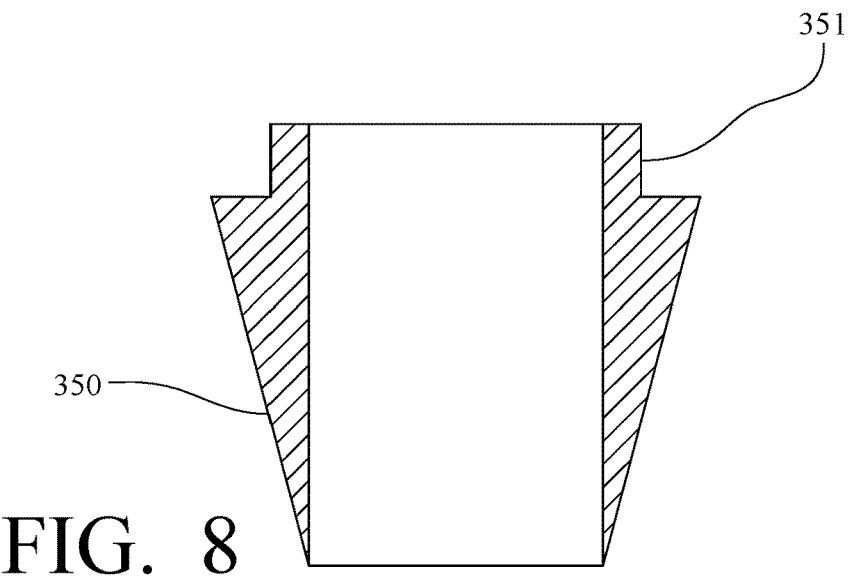
FIG. 8 is a side sectional view of the conical bearing of FIG. 6.

Referring now to FIGS. 6 and 8, the conical bearing 350 of the system 310 for intramedullary preparation further includes a distal lip 351 that keeps the cutting head 340 spaced slightly away from the conical roller bearing 350. This space prevents the leading edge 377 of the interior surface of the curved panel 376 of the follower sleeve 370 from contacting the cutting head 340 as the follower sleeve 370 is advanced.

Figure 9:
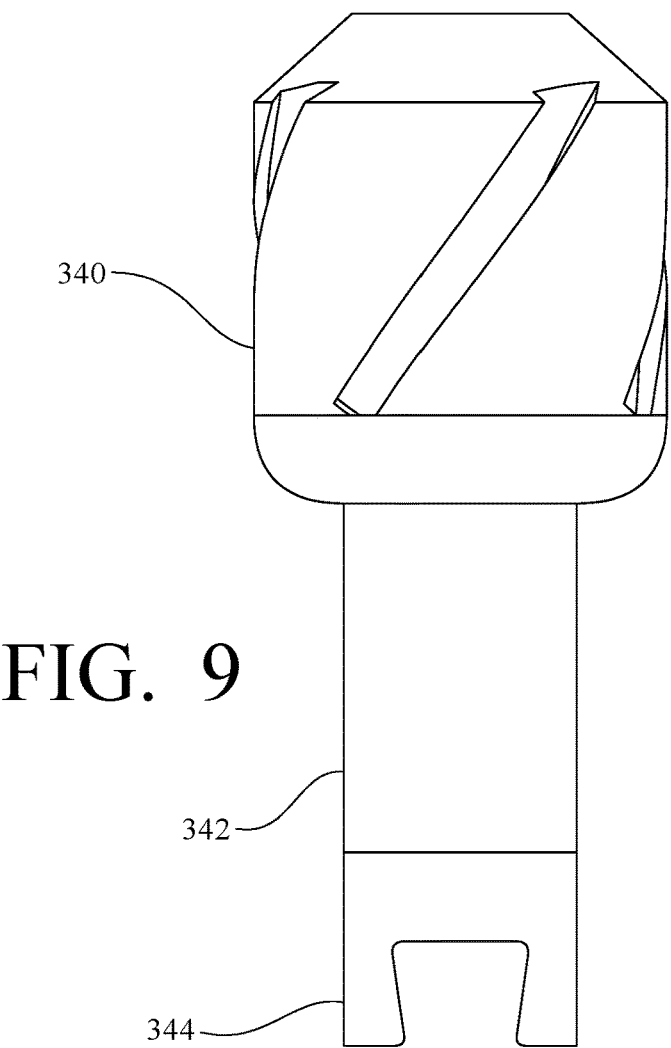
FIG. 9 is a side view of the cutting head of FIG. 6.

Referring now to FIGS. 6, 9, and 10, the cutting head 340 of the system 310 for intramedullary preparation has a shaft 342 that, as shown in FIG. 10, extends through the conical bearing 350 and terminates at a proximal end 344 which connects the cutting head 340 to the flexible drive shaft 330. Specifically, as shown in FIG. 9, a female dovetail connection is defined at the proximal end 344 of the shaft 342. This female dovetail connection is configured to mate to a male dovetail connection at the distal end 334 of the drive shaft 330 which is perhaps best shown in FIG. 6. Of course, other connections between the cutting head 340 and the drive shaft 330 are possible including permanent connections such as a weld without departing from the spirit and scope of the present invention.

As shown in FIG. 6, the flexible drive shaft 330 and the cutting head 340 of the directional reamer 320 collectively define an internal cannula 360, similar to the internal cannula 60 shown in FIG. 1, that extends through the flexible drive shaft 330 and through the cutting head 340 and through which, a guide wire 362 can extend.

Referring now to FIG. 10, in particular, the system 310 for intramedullary preparation further includes a handle 390 connected to the follower sleeve 370 with fastening screws 392. As such, the handle 390 is kept in a fixed positioned relative to the follower sleeve 370 so that, in use, the orientation of the leading edge 377 of the interior surface of the curved panel 376 is known by an operator. In particular, it is contemplated that the handle 390 points to substantially the same side as the leading edge 377, but it should be understood that the handle 390 and leading edge 377 could be kept in any orientation relative to one another. As a further refinement, although not shown, it is contemplated that the follower sleeve 370 could also include indicia that help track the distance that the follower sleeve 370 is advanced into a bone during use.

As yet another refinement, in a further embodiment of the present invention that makes use of a reamer for intramedullary preparations, and referring now to FIGS. 11-14, an exemplary system 410 for intramedullary preparation is provided that includes a reamer 420 having a flexible drive shaft 430 with a proximal end 432 and a distal end 434 opposite the proximal end 432 and a cutting head 440 mounted to the distal end 434 of the drive shaft 430. The system 410 further includes a handle 490 with a follower sleeve (or plug) 470 having a proximal end 474 connected to the handle 490 with the follower sleeve 470 extending away from the handle 490 and terminating at a distal end in the form of a collar 476. A channel 479 is defined along the length of the follower sleeve 470 which is configured to accept the drive shaft 430 such that the cutting head 440 extends forward of the collar 476. Rather than utilizing the follower sleeve 470 directly to deflect the cutting head 440 during use, the system 410 shown in FIGS. 11-14 utilizes a reaming plunger 480 that extends through the channel 479 of the follower sleeve 470 and is positioned below the drive shaft 430, as perhaps best shown in FIG. 12.

Figure 11:
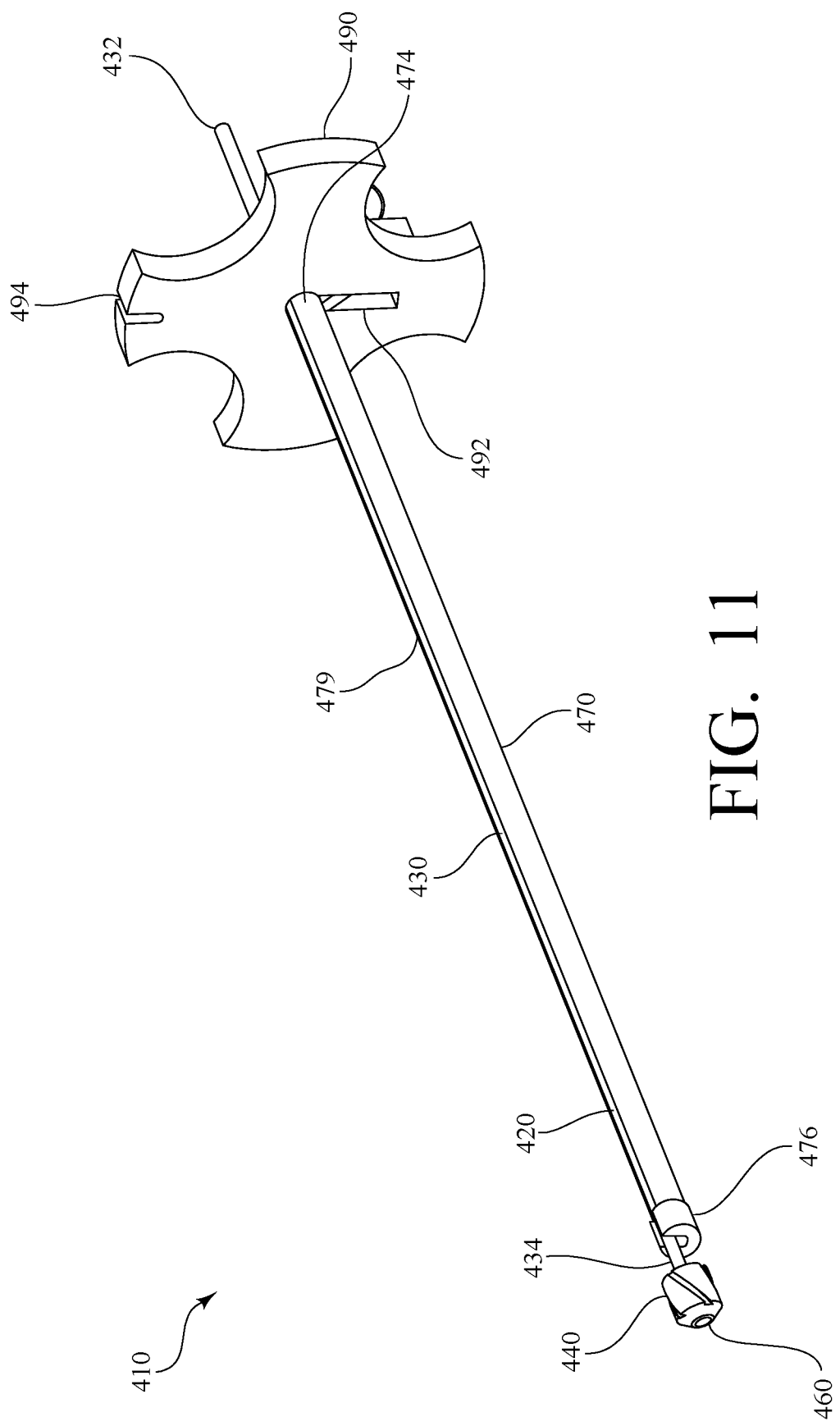
FIG. 11 is a perspective view of another system for intramedullary preparation made in accordance with the present invention and including a directional reamer, a reaming plunger, and a follower sleeve.
Figure 12:
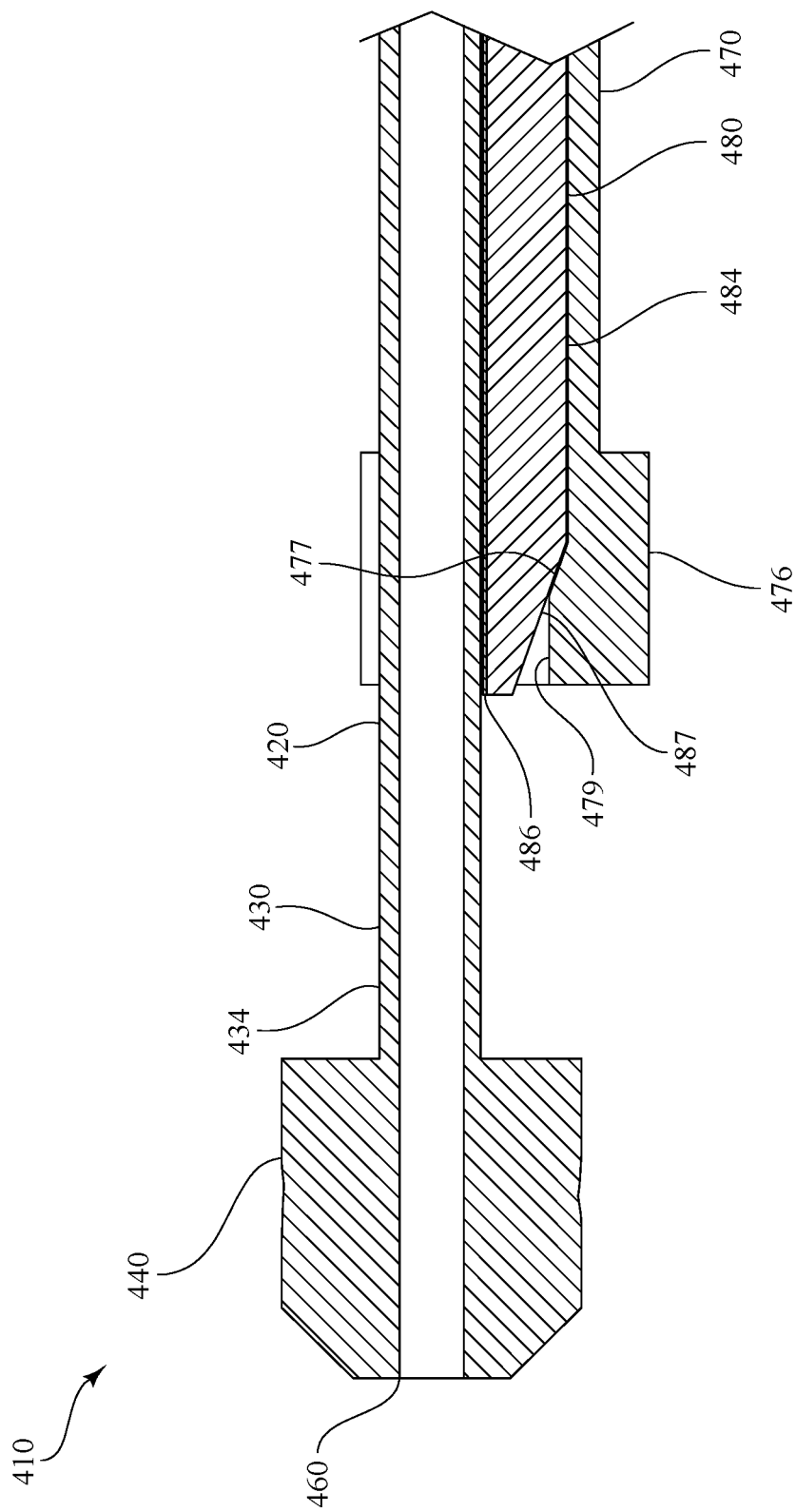
FIG. 12 is a partial sectional view of the system of FIG. 11 illustrating the interaction between the reaming plunger and the collar of the follower sleeve.
Figure 13:
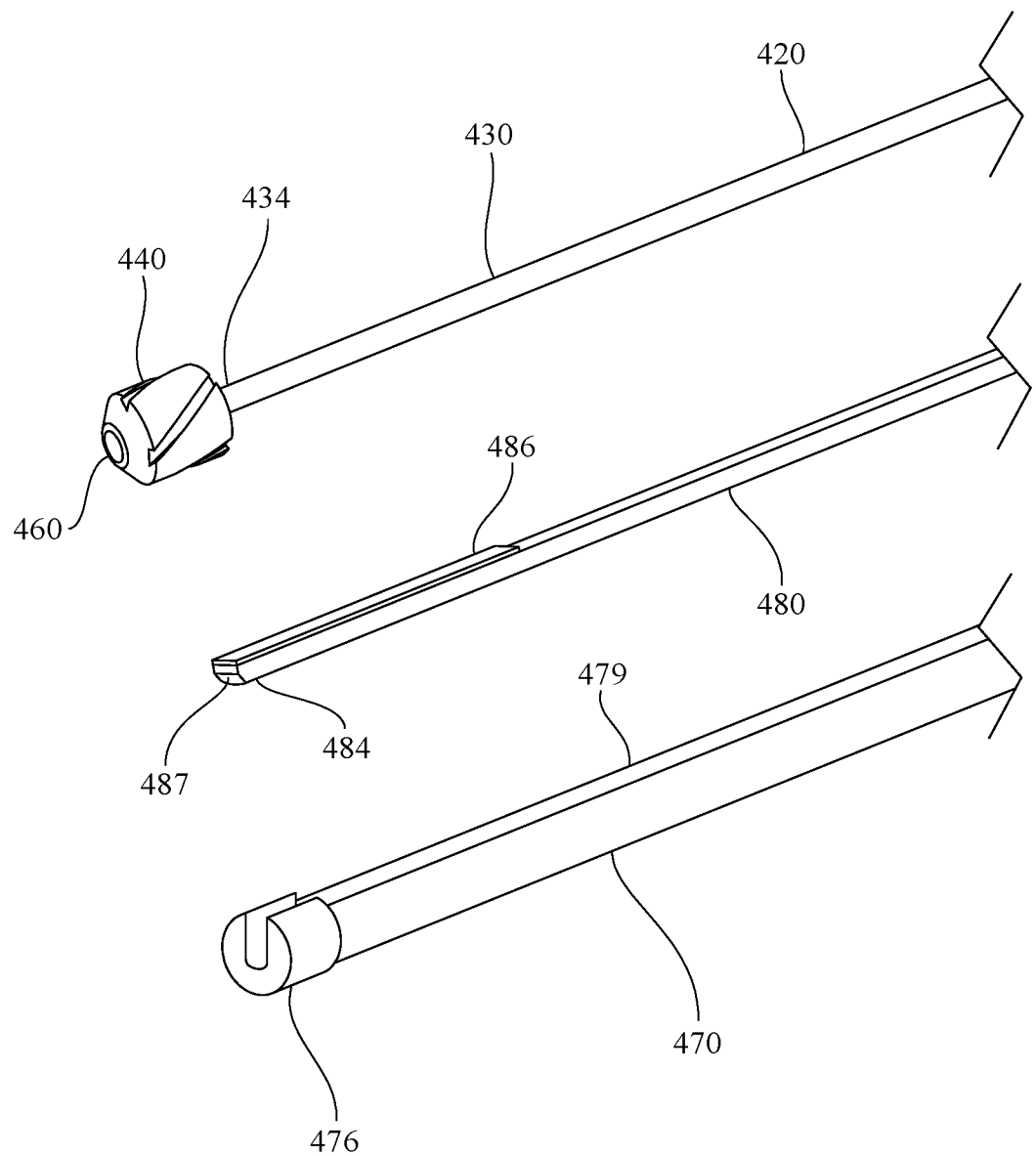
FIG. 13 is a partial exploded perspective view of the distal ends of the directional reamer, the reaming plunger, and the follower sleeve of FIG. 11.
Figure 14:
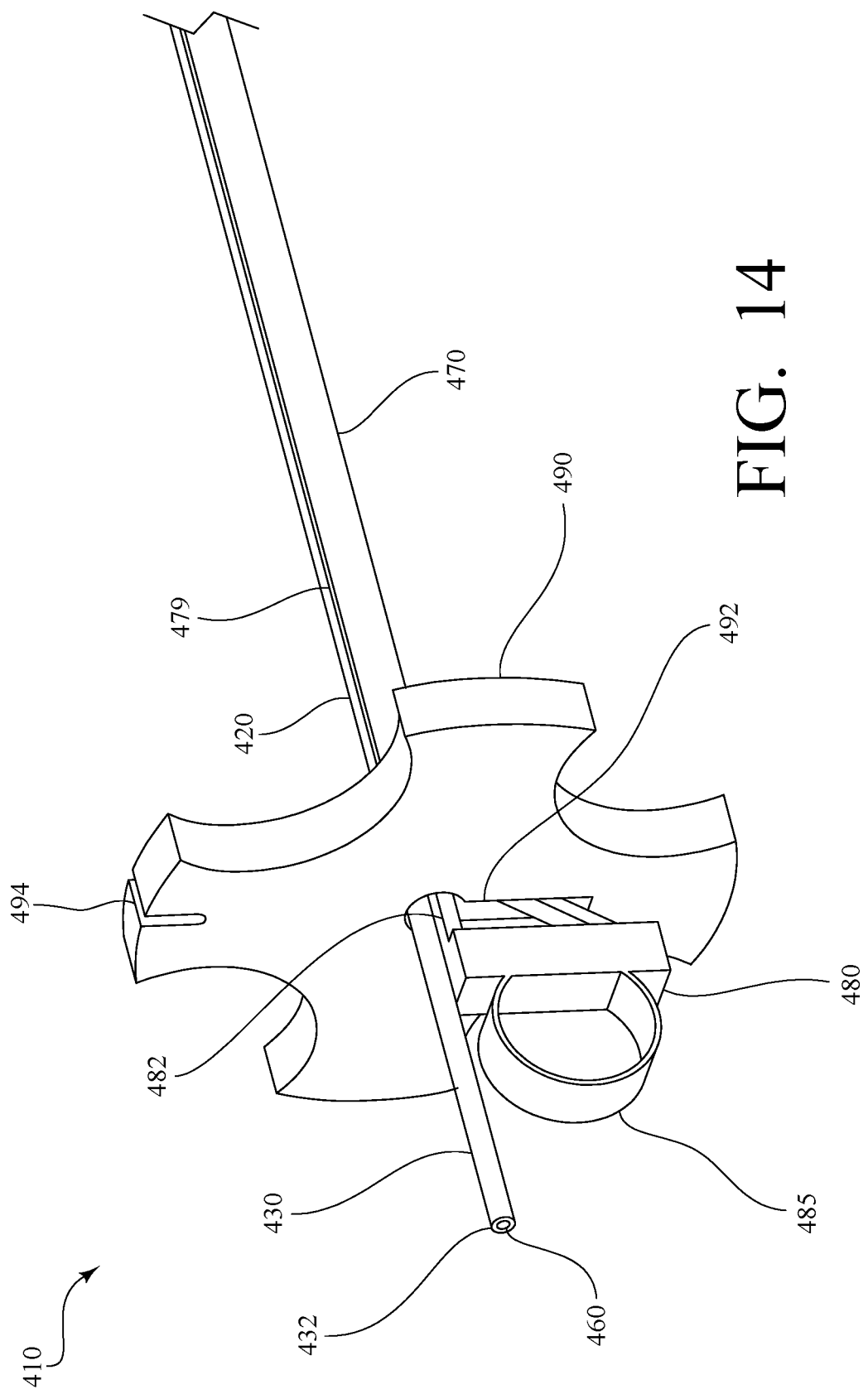
FIG. 14 is a partial rear perspective view of the system of FIG. 11.

Referring still to FIGS. 11-14, the reaming plunger 480 has a distal end 484 (shown in FIGS. 12 and 13) near the collar 476 of the follower sleeve 470 and a proximal end 482 (shown in FIG. 14) positioned near the handle 490. More specifically, as shown in FIGS. 11 and 14, the handle 490 defines a keyhole 492 and the reaming plunger 480 extends through the keyhole 492 and into the channel 479 of the follower sleeve 470. Furthermore, the reaming plunger 480 includes a handle 485 at its proximal end 482, which assists in controllably advancing the reaming plunger 480 to deflect the cutting head 440.

Referring now to FIG. 12, the distal end 484 of the reaming plunger 480 engages the collar 476 of the follower sleeve 470 to displace the distal end 434 of the flexible drive shaft 430. As shown in FIG. 12, the collar 476 defines a first sloped surface 477 that extends upward towards the end of the collar 476 (i.e., leftward in FIG. 12). The distal end 484 of the reaming plunger 480 defines a second sloped surface 487 that engages the first sloped surface 477 such that when the reaming plunger 480 is advanced (i.e., moved towards the left in FIG. 12), the second sloped surface 487 slides along the first sloped surface 477 causing the distal end 484 of the reaming plunger 480 to move outward (i.e., upward in FIG. 12) within the channel 479 of the follower sleeve 470 displacing the distal end 434 of the flexible drive shaft 430 and thus deflect the cutting head 440.

Referring now to FIGS. 12 and 13, the distal end 484 of the reaming plunger 480 further includes a cover pad 486 positioned on an upper surface of the reaming plunger 480 which acts as a bearing surface between the rotating drive shaft 430 and the reaming plunger 480. That is to say, and as perhaps best shown in FIG. 12, in operation, the drive shaft 430 rests on the cover pad 486. To this end, in some exemplary embodiments the cover pad 486 is comprised of polyether ether ketone, or PEEK, which advantageously exhibits a relatively high melting temperature and which is considered an acceptable implant material as a result of the toughness, strength, and relatively low friction provided by that material. In some exemplary embodiments, the cover pad can also be comprised of high-density or ultra-high molecular weight polyethylene (UHMWPE).

Referring now to FIGS. 11 and 14, the handle 490 is designed to be rotatable as the reamer 420 is advanced through the medullary canal in a bone so that the channel 479 of the follower sleeve 470 opens in a desired direction. The handle 490 includes a notch 494 formed on the same side as the channel 479 of the follower sleeve 470, and preferably the follower sleeve 470 is fixed to the handle 490 such that the notch 494 is kept in a fixed positioned relative to the channel 479. In this way, the orientation of the channel 479 is known by an operator during use so that, when the reaming plunger 470 is advanced, the cutting head 440 will be deflected in the desired direction, allowing for eccentric cutting by the cutting head 440.

It is contemplated that in this exemplary embodiment the flexible drive shaft 430 has a diameter of about 4 mm whereas the cutting head 440 has a diameter of about 12 mm. Of course, other diameters are also possible without departing from the spirit and scope of the present invention. In fact, it is contemplated that in some embodiments, the cutting head 440 can be modular and replaced in order to use a cutting head with a preferred diameter and/or other attribute. In any event, as shown in FIGS. 11-14, the flexible drive shaft 430 and the cutting head 440 of the directional reamer 420 collectively define an internal cannula 460, similar to the internal cannula 60 shown in FIG. 1, that extends through the flexible drive shaft 430 and through the cutting head 440 and through which, a guide wire (not shown) can extend.

Figure 17:
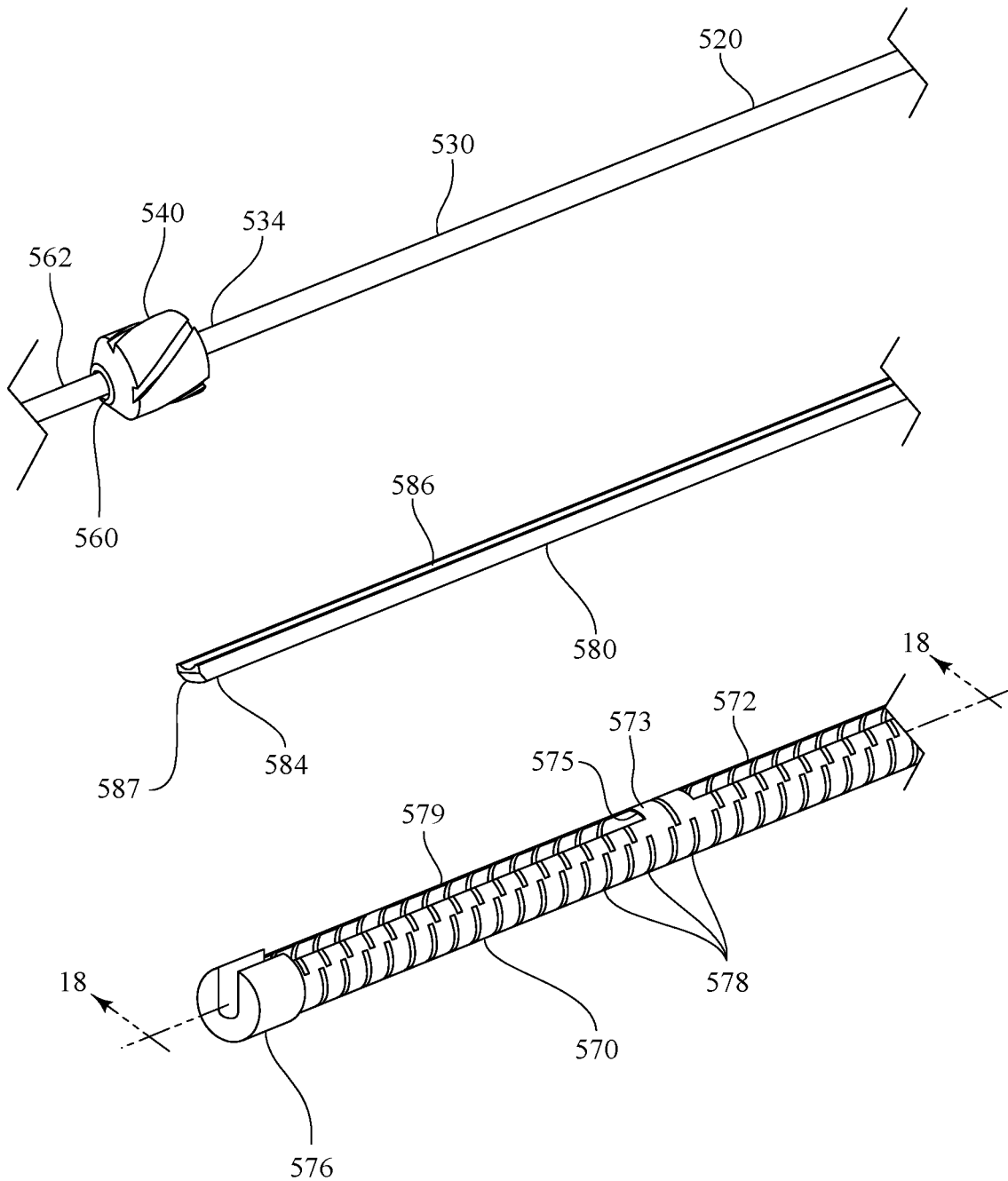
FIG. 17 is a partial exploded perspective view of the distal ends of the directional reamer, the reaming plunger, and the follower sleeve of FIG. 15.

As yet another refinement, in a further embodiment of the present invention that makes use of a reamer for intramedullary preparations, and referring now to FIGS. 15-17, an exemplary system 510 for intramedullary preparation is provided that includes a reamer 520 having a flexible drive shaft 530 and a cutting head 540 mounted to the distal end 534 of the drive shaft 530. The system 510 further includes a follower sleeve (or plug) 570 having a proximal end 574 (shown in FIG. 21) and a distal end in the form of a collar 576. A channel 579 is defined along the length of the follower sleeve 570 which is configured to accept the drive shaft 530 such that the cutting head 540 extends forward of the collar 576. Furthermore, a reaming plunger 580 extends through the channel 579 of the follower sleeve 570 and is positioned below the drive shaft 530.

As shown in FIGS. 15-17, the flexible drive shaft 530 and the cutting head 540 of the directional reamer 520 collectively define an internal cannula 560, similar to the internal cannula 60 shown in FIG. 1, that extends through the flexible drive shaft 530 and through the cutting head 540 and through which, a guide wire 562 can extend.

Referring now to FIGS. 15-19, the distal end 584 of the reaming plunger 580 engages the collar 576 of the follower sleeve 570 to displace the distal end 534 of the flexible drive shaft 530. As shown in FIGS. 15 and 16, the collar 576 defines a first sloped surface 577 that extends upward towards the end of the collar 576 (i.e., leftward in FIGS. 15 and 16). The distal end 584 of the reaming plunger 580 defines a second sloped surface 587 that engages the first sloped surface 577 such that when the reaming plunger 580 is advanced, as shown in FIG. 16, the second sloped surface 587 slides along the first sloped surface 577 causing the distal end 584 of the reaming plunger 580 to move outward within the channel 579 of the follower sleeve 570 displacing the distal end 534 of the flexible drive shaft 530 and thus deflect the cutting head 540. In some embodiments, the first and second sloped surfaces 577, 587 are formed at approximately 30° angles, but other inclines are contemplated.

Referring now to FIGS. 17 and 19, the reaming plunger 580 further includes a concave upper surface 586 which acts as a bearing surface between the rotating drive shaft 530 and the reaming plunger 580. That is to say, in operation, the drive shaft 530 rests partially within the concave upper surface 586 of the reaming plunger 580. To this end, in some exemplary embodiments, the reaming plunger 580 is comprised, at least in part, of polyether ether ketone, or PEEK, which advantageously exhibits a relatively high melting temperature and which is considered an acceptable implant material as a result of the toughness, strength, and relatively low friction provided by that material. Furthermore, PEEK provides sufficient flexibility for the reaming plunger 580 to accommodate a curved femur. In some exemplary embodiments, the cover pad can also be comprised of high-density or ultra-high molecular weight polyethylene (UHMWPE). Furthermore, the exemplary directional reamer 520 shown in FIGS. 15-17 includes a sleeve 538 that is also made of PEEK and substantially surrounds the drive shaft 530.

Referring now to FIGS. 16-18, the channel 579 of the exemplary follower sleeve 570 includes not only an open top 572 along substantially the entire length of the follower sleeve 570, but also an open bottom 571 along substantially the entire length of the follower sleeve 570. The open bottom 571 of the follower sleeve 570 allows for the follower sleeve 570 to accommodate the reaming plunger 580 such that a rounded bottom surface 588 (shown in FIG. 19) of the reaming plunger 580 is substantially flush with the exterior of the follower sleeve 570, and therefore providing easier insertion of the reaming system 510 through the medullary canal.

Referring now to FIGS. 17 and 18, one or more bands 573 span across the open top 572 of the channel 579, and at least the band 573 closest to the collar 567 includes a fluted forward edge 575, as perhaps best shown in FIG. 18. It is contemplated that the fluted forward edge 575 prevents wear on the drive shaft 530. In particular, when the reaming plunger 580 displaces the distal end 534 of the drive shaft 530, the drive shaft 530 will come into contact with the band 573 while spinning. The fluted forward edge 575 prevents the drive shaft 530 from rubbing against a sharp edge.

Referring now to FIGS. 16-18, the follower sleeve 570 further includes a plurality of quadrant cuts (or fenestrations) 578 along the length of the follower sleeve 570, which provide the follower sleeve 570 an amount of flexibility to accommodate a curved femur.

Figure 20:
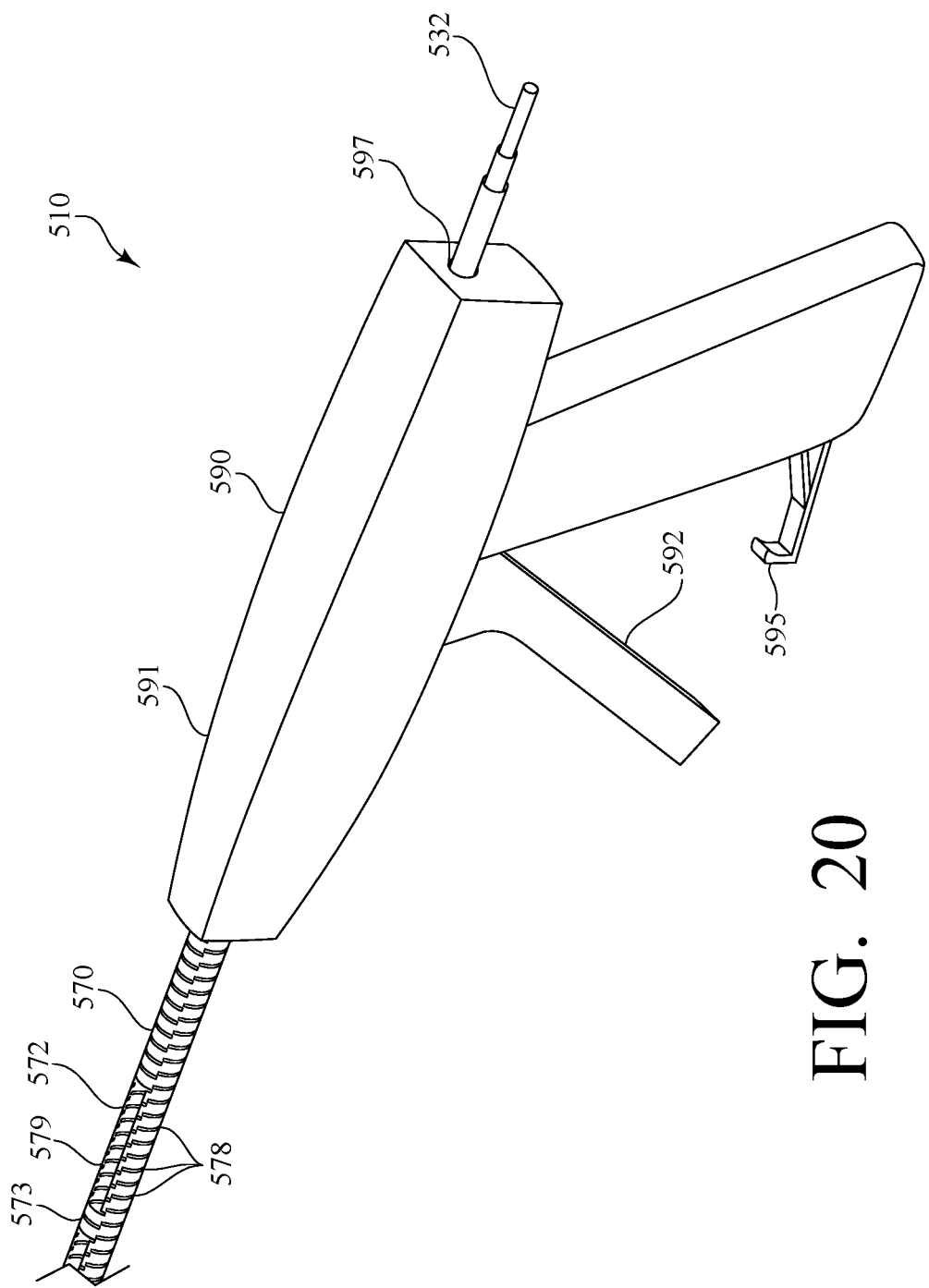
FIG. 20 is a rear perspective view of the proximal end of the system of FIG. 15.
Figure 21:
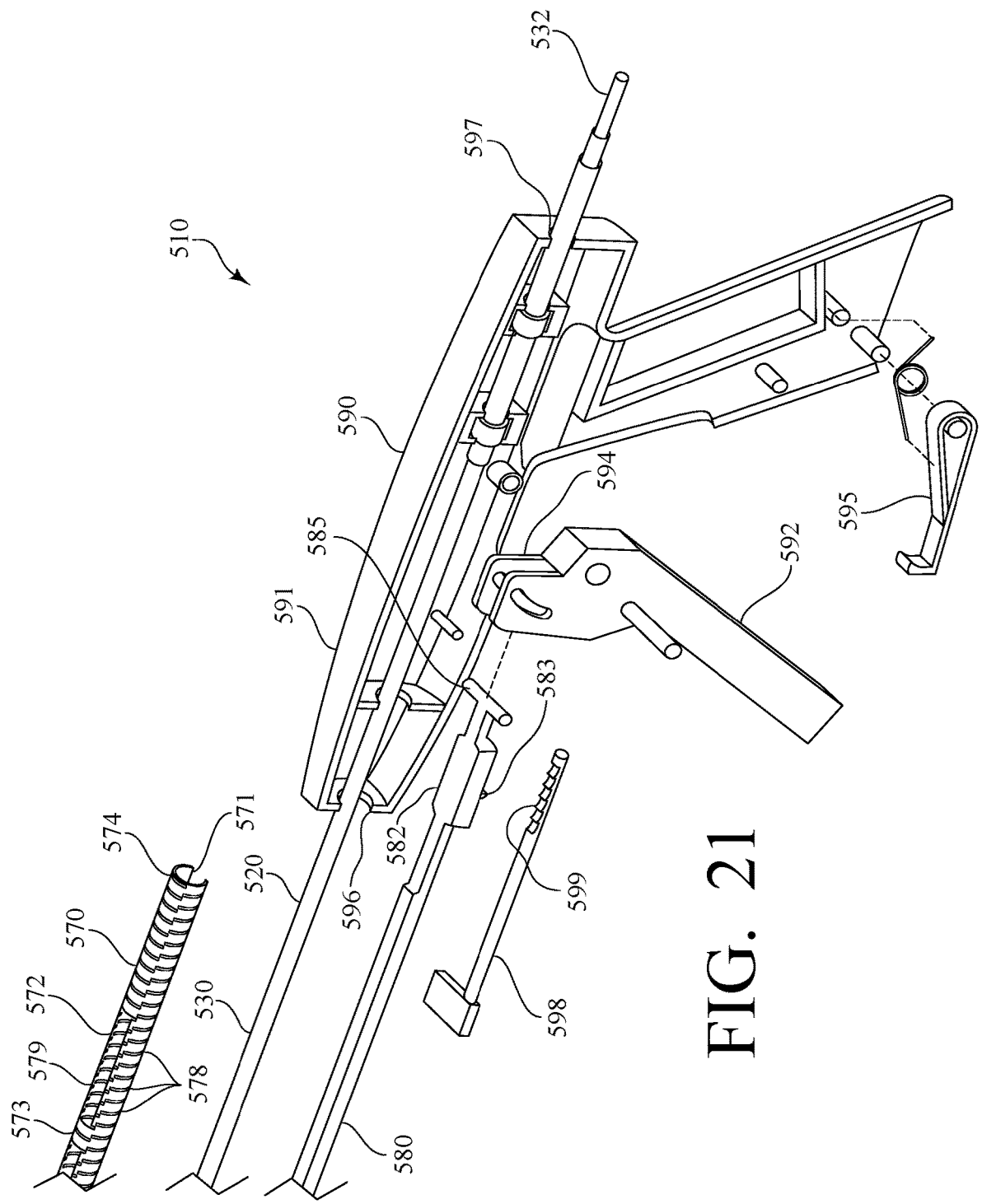
FIG. 21 is a partial exploded rear perspective view of the proximal end of the system of FIG. 15.

Referring now to FIGS. 20 and 21, the system 510 further comprises a handle 590 that is operably attached to the follower sleeve 570 and configured to controllably advance the reaming plunger 580 relative to the follower sleeve 570 to thereby deflect the cutting head 540 of the direction reamer 520. As shown in FIG. 20, the handle 590 includes a housing 591, a lever 592, and a lever lock 595, as discussed further below.

Referring now specifically to FIG. 21, the housing 591 defines a forward opening 596 and a rear opening 597 opposite the forward opening. The reamer 520, the follower sleeve 570, and the reaming plunger 580 all enter through the forward opening 596, but only the reamer 520 exits through the rear opening 597. In particular, a proximal end 532 of the drive shaft 530 protruding through the rear opening 597 of the housing 591 provides a means for attaching a drill or the like to the proximal end 532 of reamer 520. A proximal end 574 of the follower sleeve 570 is connected to the housing 591 itself, whereas a proximal end 582 of the reaming plunger 580 is connected to the lever 592. More specifically, the proximal end 582 of the reaming plunger 580 includes a t-shaped engagement flange 585 which is pivotally connected to an upper portion 594 of the lever 592. As such, when the lever 592 is pulled towards the handle 590, the upper portion 594 of the lever 592 pushing the reaming plunger 580 forward relative to the follower sleeve 570.

Referring still to FIG. 21 in particular, the proximal end 582 of the reaming plunger 580 further includes a locking tooth 583 configured to selectively engage a ratcheting member 598 located inside the housing 591 of the handle 590. More specifically, the ratcheting member 598 includes a plurality of teeth 599 which, when the reaming plunger 580 is moved forward, successively engage the locking tooth 583 to hold the reaming plunger 580 in its forward most position. In order to release the reaming plunger 580, a user simply twists the ratcheting member 598 by the end accessible at the front of the handle 590. Likewise, the handle 590 further includes a lever lock 595 configured to engage and hold the lever 592 when fully pulled.

Each of the exemplary systems described herein can also be used as part of a method for fixing a bone in a subject, including both human and animal subjects. In some implementations, an exemplary method for fixing a bone in a subject includes first providing a directional reamer having a flexible drive shaft with a proximal end and a distal end, a cutting head operably connected to the distal end of the flexible drive shaft, and a conical bearing operably connected to the distal end of the flexible drive shaft adjacent to the cutting head. A follower sleeve can then be provided that has a distal end configured to engage and displace the conical bearing and a hollow interior with a diameter sufficient for surrounding the flexible drive shaft of the directional reamer. The flexible drive shaft is then inserted into the follower sleeve, and the directional reamer and follower sleeve are subsequently placed into a medullary canal of a bone. Upon initial placement into a medullary canal, and depending on the overall anatomy of the bone or the geometry of a particular bone fracture being treated, the follower sleeve is then selectively advanced along the length of the flexible drive shaft such that the distal end of the follower sleeve contacts the conical bearing and deflects the cutting head of the directional reamer to the extent desired.

In some other embodiments, an exemplary method for fixing a bone in a subject includes first providing a directional reamer, the directional reamer including a flexible drive shaft have a proximal end and a distal end and a cutting head operably connected to the distal end of the flexible drive shaft. A follower sleeve (or plug) extending from a handle and terminating at a collar can then be provided with the follower sleeve defining a channel configured to accept the flexible drive shaft. A reaming plunger can then be provided that extends through the channel of the follower sleeve and is positioned below the flexible drive shaft. The flexible drive shaft is then inserted into the channel of the follower sleeve such that the cutting head extends forward of the collar. Upon initial placement into a medullary canal, and depending on the overall anatomy of the bone or the geometry of a particular bone fracture being treated, the reaming plunger is then selectively advanced along the channel of the follower sleeve such that a distal end of the reaming plunger engages the collar of the follower sleeve to displace the distal end of the flexible drive shaft. This, in turn, deflects the cutting head of the directional reamer to the extent desired.

By selectively deflecting the cutting head of the directional reamer in such a manner as described above, a medullary canal can thus be selectively shaped in a particular bone that will correspond to that particular bone's anatomy or to the fracture geometry found in that particular bone.

Throughout this document, various references are mentioned. All such references are incorporated herein by reference, including the references set forth in the following list:

REFERENCES

1. U.S. Pat. No. 4,646,738 to Trott.
2. U.S. Pat. No. 5,591,170 to Spievack, et al.
3. U.S. Pat. No. 7,749,225 to Chappuis, et al.
4. U.S. Pat. No. 5,928,239 to Mirza.
5. U.S. Pat. No. 5,062,845 to Kuslich, et al.
6. U.S. Pat. No. 5,431,671 to Nallakrishnan.
7. U.S. Pat. No. 6,332,886B1 to Green, et al.
8. U.S. Pat. No. 5,908,423 to Kashuba, et al.
9. U.S. Pat. No. 6,383,188 to Kuslich.

One of ordinary skill in the art will recognize that additional embodiments are also possible without departing from the teachings of the present invention or the scope of the claims which follow. This detailed description, and particularly the specific details of the exemplary embodiments disclosed herein, is given primarily for clarity of understanding, and no unnecessary limitations are to be understood therefrom, for modifications will become apparent to those skilled in the art upon reading this disclosure and may be made without departing from the spirit or scope of the claimed invention.

What is claimed is:

1. A system for intramedullary preparations, the system comprising:
   a directional reamer, comprising:
      a flexible drive shaft having a proximal end and a distal end;
      a cutting head operably connected to the distal end of the flexible drive shaft; and
      a conical roller bearing, which is operably connected to the distal end of the flexible drive shaft adjacent to the cutting head and comprises:
         a cavity, through which the flexible drive shaft extends and in which the distal end of the flexible drive shaft is rotatably positioned;
         a first set of rollers that are arranged circumferentially around the flexible drive shaft, within a space defined between an outer circumferential surface of the flexible drive shaft and an inner surface of the cavity; and
         a second set of rollers that are arranged circumferentially around the flexible drive shaft, within a space defined between a distal end of the conical roller bearing and a proximal end of the cutting head;
      wherein the proximal end of the cutting head is adjacent to the proximal end of the cutting head;

a follower sleeve having a proximal end and a distal end in the form of a collar, the follower sleeve defining a channel configured to accept the flexible drive shaft; and a reaming plunger extending through the channel of the follower sleeve and positioned adjacent to the flexible drive shaft, the reaming plunger configured to engage the collar of the follower sleeve to displace the distal end of the flexible drive shaft and deflect the cutting head.

2. The system of claim 1, wherein the collar defines a first sloped surface and the reaming plunger defines a second sloped surface that engages the first sloped surface such that, when the reaming plunger is advanced along the channel, the second sloped surface slides along the first sloped surface causing the reaming plunger to move outward within the channel of the follower sleeve.

3. The system of claim 1, wherein the flexible drive shaft, the reaming plunger, or both the flexible drive shaft and the reaming plunger are comprised of polyether ether ketone.

4. The system of claim 1, wherein the reaming plunger defines a concave upper surface and the flexible drive shaft rests on the concave upper surface.

5. The system of claim 1, wherein the reaming plunger further includes a cover pad positioned on an upper surface of the reaming plunger such that the flexible drive shaft rests on the cover pad.

6. The system of claim 1, wherein the flexible drive shaft and the cutting head collectively define an internal cannula extending through the flexible drive shaft from the proximal end to the distal end of the flexible drive shaft and through the cutting head.

7. The system of claim 6, wherein the internal cannula has a diameter sufficient to surround a guide wire.

8. The system of claim 1, wherein the follower sleeve is flexible.

9. The system of claim 1, wherein the channel of the follower sleeve has an open bottom along substantially the entire length of the follower sleeve and an open top along substantially the entire length of the follower sleeve.

10. The system of claim 9, wherein the follower sleeve includes one or more bands spanning across the open top of the channel.

11. The system of claim 10, wherein at least one of the one or more bands includes a fluted forward edge, the fluted forward edge configured to engage the flexible drive shaft when the reaming plunger displaces the distal end of the flexible drive shaft and deflects the cutting head.

12. The system of claim 1, further comprising a drill connected to the proximal end of the flexible drive shaft.

13. The system of claim 1, further comprising a handle operably attached to the follower sleeve, the handle configured to advance the reaming plunger relative to the follower sleeve to thereby deflect the cutting head of the directional reamer.

14. The system of claim 13, wherein the handle includes a lever for advancing the reaming plunger, the lever including an upper portion secured to a proximal end of the reaming plunger.

15. The system of claim 14, wherein the handle further includes a locking mechanism to maintain a position of the lever.

16. A method for fixing a bone in a subject, the method comprising:

providing a directional reamer, the directional reamer comprising:

a flexible drive shaft having a proximal end and a distal end;

a cutting head operably connected to the distal end of the flexible drive shaft; and a conical roller bearing, which is operably connected to the distal end of the flexible drive shaft adjacent to the cutting head and comprises:

a cavity, through which the flexible drive shaft extends and in which the distal end of the flexible drive shaft is rotatably positioned;

a first set of rollers that are arranged circumferentially around the flexible drive shaft, within a space defined between an outer circumferential surface of the flexible drive shaft and an inner surface of the cavity; and a second set of rollers that are arranged circumferentially around the flexible drive shaft, within a space defined between a distal end of the conical roller bearing and a proximal end of the cutting head;

wherein the proximal end of the cutting head is adjacent to the proximal end of the cutting head;

providing a follower sleeve having a proximal end and a distal end in the form of a collar, the follower sleeve defining a channel configured to accept the flexible drive shaft;

providing a reaming plunger configured to extend through the channel of the follower sleeve;

inserting the reaming plunger within the channel of the follower sleeve and positioned adjacent to the flexible drive shaft;

inserting the flexible drive shaft into the follower sleeve adjacent to the reaming plunger and such that the cutting head extends forward of the collar of the follower sleeve;

placing the directional reamer containing the reaming plunger and the follower sleeve into a medullary canal of a bone; and advancing the reaming plunger along the channel of the follower sleeve such that a distal end of the reaming plunger engages the collar of the follower sleeve to displace the distal end of the flexible drive shaft and deflect the cutting head.

17. The method of claim 16, wherein the bone is a long bone.

18. A directional reamer, comprising:

a flexible drive shaft having a proximal end and a distal end;

a cutting head operably connected to the distal end of the flexible drive shaft; and a conical roller bearing, which is operably connected to the distal end of the flexible drive shaft adjacent to the cutting head and comprises:

a cavity, through which the flexible drive shaft extends and in which the distal end of the flexible drive shaft is rotatably positioned;

a first set of rollers that are arranged circumferentially around the flexible drive shaft, within a space defined between an outer circumferential surface of the flexible drive shaft and an inner surface of the cavity; and a second set of rollers that are arranged circumferentially around the flexible drive shaft, within a space defined between a distal end of the conical roller bearing and a proximal end of the cutting head;

wherein the proximal end of the cutting head is adjacent to the proximal end of the cutting head.

19. The directional reamer of claim 18, wherein the flexible drive shaft and the cutting head collectively define an internal cannula extending through the flexible drive shaft from the proximal end to the distal end of the flexible drive shaft and through the cutting head.

20. The directional reamer of claim 19, wherein the internal cannula has a diameter sufficient to surround a guide wire.

21. The directional reamer of claim 18, wherein the first set of rollers is operably connected to the flexible drive shaft and the second set of rollers is operably connected to the cutting head.

22. The directional reamer of claim 21, wherein the conical roller bearing includes an exterior post that extends in a radial direction of the conical roller bearing, the radial direction of the conical roller bearing being defined in a plane that is perpendicular to a longitudinal axis of the conical roller bearing.

23. A system for intramedullary preparations, the system comprising:
    a directional reamer, comprising:
        a flexible drive shaft having a proximal end and a distal end,
        a cutting head operably connected to the distal end of the flexible drive shaft, and
        a conical roller bearing, which is operably connected to the distal end of the flexible drive shaft adjacent to the cutting head and comprises:
            a cavity, through which the flexible drive shaft extends and in which the distal end of the flexible drive shaft is rotatably positioned;
            a first set of rollers that are arranged circumferentially around the flexible drive shaft, within a space defined between an outer circumferential surface of the flexible drive shaft and an inner surface of the cavity; and
            a second set of rollers that are arranged circumferentially around the flexible drive shaft, within a space defined between a distal end of the conical roller bearing and a proximal end of the cutting head;
            wherein the proximal end of the cutting head is adjacent to the proximal end of the cutting head; and
    a follower sleeve defining a hollow interior and having a proximal end and a distal end, the hollow interior having a diameter sufficient for surrounding the flexible drive shaft of the directional reamer, and the distal end of the follower sleeve configured to contact the conical roller bearing and deflect the cutting head.

24. The system of claim 23, wherein the distal end of the follower sleeve is comprised of a semi-circular curved panel with a leading edge configured to contact the conical roller bearing and deflect the cutting head.

\* \* \* \* \*